United States Patent
Hsieh et al.

(10) Patent No.: US 8,461,282 B2
(45) Date of Patent: Jun. 11, 2013

(54) (PENTAPHENYL)PHENYL GROUP CONTAINING COMPOUND, POLYMERIC DERIVATIVE THEREOF AND METHOD FOR FORMING THE SAME

(75) Inventors: Kuo-Huang Hsieh, Taipei (TW); Man-Kit Leung, Taipei (TW); Wen-Chang Chen, Taipei (TW); Chao-Hui Kuo, Taipei (TW); Hong-Jun Chen, Taipei (TW); Hsin-Chung Ke, Taipei (TW); Cheng-Hsiu Ku, Taipei (TW)

(73) Assignee: National Taiwan University, Taipei (TW)

( * ) Notice: Subject to any disclaimer, the term of this patent is extended or adjusted under 35 U.S.C. 154(b) by 554 days.

(21) Appl. No.: 12/629,648

(22) Filed: Dec. 2, 2009

(65) Prior Publication Data
US 2010/0137461 A1    Jun. 3, 2010

Related U.S. Application Data

(62) Division of application No. 11/751,634, filed on May 22, 2007, now abandoned.

(51) Int. Cl.
*C08G 16/02* (2006.01)
*C08G 61/12* (2006.01)

(52) U.S. Cl.
USPC ............ 528/7; 528/5; 528/239; 257/E25.007; 257/40; 257/E51.028

(58) Field of Classification Search
USPC ................... 528/5, 7, 239; 257/40, E25.007, 257/E51.028
See application file for complete search history.

(56) References Cited

FOREIGN PATENT DOCUMENTS
JP      2004244400    9/2004
KR          681474    2/2007
WO      2006077130    7/2006

OTHER PUBLICATIONS

Suzuki, A. "Chapter III.2.2 Overview of the Suzuki Protocol with B" in Handbook of Organopalladium Chemistry for Organic Synthesis, Negishi, E. ed. 2002 John Wiley & Sons, 249-262.*
Boutagy et. al. "Olefin Synthesis with Organic Phosphonate Carbanions" Chemical Reviews, 1974, vol. 74, No. 1 87-99.*
Watanabe et al. "Hexaphenylbenzene Derivatives for Blue Organic Light-emitting Devices" Chemistry Letters, Mar. 29, 2007, 36, 590-591.

* cited by examiner

*Primary Examiner* — David K O Dell
(74) *Attorney, Agent, or Firm* — WPAT, PC; Justin King

(57) ABSTRACT

The present invention discloses an iridium complex containing a (pentaphenyl)phenyl ligand, having the following general equation:

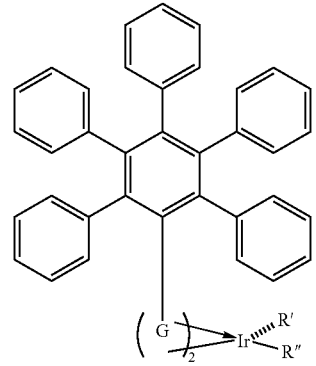

in which G is primary ligand, R' and R" are auxiliary ligands. On the other hand, the present invention discloses a compound with a 9-[(pentaphenyl)phenyl]carbazole structure and its polymeric derivative.

4 Claims, 6 Drawing Sheets

(PENTAPHENYL)PHENYL GROUP CONTAINING COMPOUND, POLYMERIC DERIVATIVE THEREOF AND METHOD FOR FORMING THE SAME

BACKGROUND OF THE INVENTION

1. Field of the Invention

The present invention is generally related to a compound containing (pentaphenyl)phenyl group, and more particularly to a compound containing (pentaphenyl)phenyl group, used as an organic display material, and its polymeric derivative and a method for forming the same.

2. Description of the Prior Art

Organic light emitting diode displays, also known as organic electroluminescent displays (referred to as "OEL display") have advantages of self-emitting, quick response time, wide viewing angle, simple fabricating processes, and being flexible. Luminance mechanism of organic electroluminescence is similar to that of inorganic light emitting diodes. Generally, organic light emitting diodes can be divided into two categories: small molecule organic light emitting diodes and polymer organic light emitting diodes. For small molecule organic light emitting diodes, small molecule dyes or pigments are the major compositions. For polymer organic light emitting diodes, conjugated macromolecule organic materials are the major compositions.

For small molecule dyes or pigments, polymeric light emitting materials, hole injection materials, hole transport materials, the common drawback is that the glass transition temperature is too low. Since the OEL device produces excess joule heat during operating for a long period of time, the operating temperature of the device generally exceeds the Tg of the material so as to cause the material to recrystallize and thereby to result in brightness decay and shortened lifetime. In light of the above background, it is necessary to develop a novel material for organic light emitting diodes so as to provide an excellent product with good thermal stability, high luminance efficiency, and being unlikely to crystallize. Therefore, the utilization lifetime can be prolonged and the luminance efficiency can be increased.

SUMMARY OF THE INVENTION

In light of the above background, in order to fulfill the requirements of the industry, the present invention provides a new compound containing (pentaphenyl)phenyl group, used as an organic display material, and its polymeric derivative and a method for forming the same.

One object of the present invention is to introduce a (pentaphenyl)phenyl substituent to an iridium phosphorescent material to have intermolecular energy transfer become intramolecular energy transfer so as to increase efficiency in energy transfer and luminance efficiency. At the same time, by enhancing steric effect, queching effect caused by concentration can be reduced.

Another object of the present invention is to adjust the lighting color of a phosphorescent material by modifying the substituent on phenyl-pyridines.

Another object of the present invention is to obtain polymer electroluminescent materials by using 9-[(pentaphenyl)phenyl]carbazole, as a major substance, together with fluorene having a long alkyl side chain and carbazole, being as monomers, to carry out polymerization, using Suzuki coupling and Horner-Wadsworth-Emmons (HWE) reactions. Furthermore, 1,4-bis(2-bromostyryl)benzene (OPV) and benzothiazole are introduced to improved the optical and electrical property of the polymers. In thermal property, the (pentaphenyl)phenyl group side chain structure increases the steric effect of polymers so as to reduce molecular symmetry and reduce molecular chain aggregation to thereby prevent from being over red-shifted in fluorescence. On the other hand, the (pentaphenyl)phenyl group side chain structure makes the rotational degree of freedom decreased. Therefore, the glass transition temperature of the polymer provided by the present invention is higher than that of the general carbazole polymer. The polymer provided by the present invention has excellent thermal stability. Therefore, this present invention does have the economic advantages for industrial applications.

Accordingly, the present invention discloses an iridium complex containing a (pentaphenyl)phenyl ligand, having the following general equation:

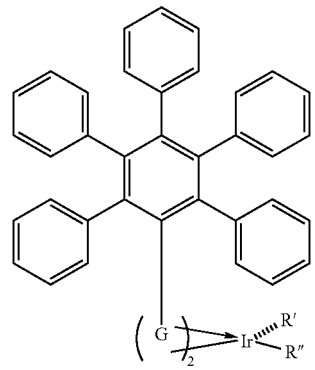

in which G is primary ligand, R' and R" are auxiliary ligands. On the other hand, the present invention discloses a compound with a 9-[(pentaphenyl)phenyl]carbazole structure and its polymeric derivative.

DESCRIPTION OF THE PREFERRED EMBODIMENTS

Figure 1:
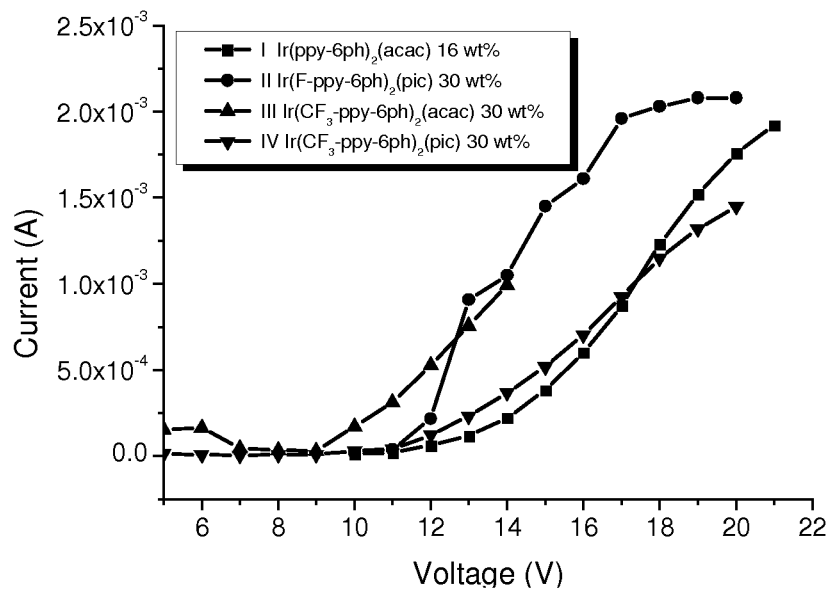
FIG. 1 shows voltage-current curves for the devices I, II, III, and IV according to the example 3 of the present invention.

What is probed into the invention is a compound containing (pentaphenyl)phenyl group, its polymeric derivative, and a method for forming the same. Detail descriptions of the processes and elements will be provided in the following in order to make the invention thoroughly understood. Obviously, the application of the invention is not confined to specific details familiar to those who are skilled in the art. On the other hand, the common processes and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Recently, cyclic iridium complexes become a breakthrough phosphorescent material. The device using such material has distinct characteristics, compared to the device using pure organic molecules. Red and green emitting materials have been satisfactorily developed while the blue emitting material is still very difficult to be developed.

Generally, for a blue phosphorescent molecule, 2-(2,4-difluorophenyl)-pyridine is the core of the ligand in the iridium complex. FIrpic, iridium (III) bis(4,6-difluorophenylpyridinato)picolate, is the most well-known one. In a device structure like [ITO/CuPc (10 nm)/α-NPD (30 nm)/FIrpic:CBP (6 wt %) (30 nm)/LiF (1 nm)/Al (100 nm)], when the high current $J=100$ mA/cm$^2$, the maximum luminance is 6400 cd/m$^2$, the maximum external quantum efficiency is about 3.0%, the wavelengths at the maximum intensity are 495 and 540 nm, and the CIE coordinate (x, y)=(0.16, 0.29). The maximum external quantum efficiency is about 10% and the maximum luminance efficiency is 10 lm/W. When the emission wavelength is at 470 nm, there is good efficiency but it shows an obvious vibration structure in the spectrum, which exists the problem of having double peaks to result in less color saturation with CIE coordinate (x, y)=(0.17, 0.34). Depending on the sensitivity of human eyes, the color is like blue-green. Besides, recently FIr6, iridium( )bis-(4',6'-difluorophenylpyridinato)tetrakis(1-pyrazolyl)boratethe, possibly becomes the second practical blue phosphorescent material, whose maximum external quantum efficiency is about 9-10%, maximum luminance efficiency is 11-14 lm/W, and CIE coordinate (x, y)=(0.16, 0.26) has great improvement.

In a first embodiment of the present invention, an iridium complex containing (pentaphenyl)phenyl group is provided having the following general equation:

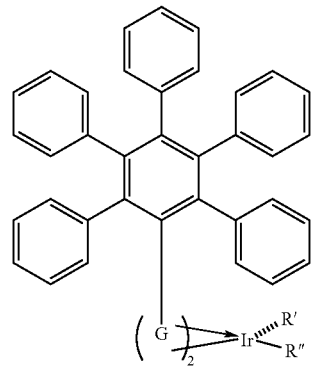

wherein G comprises one selected from the group consisting of the following:

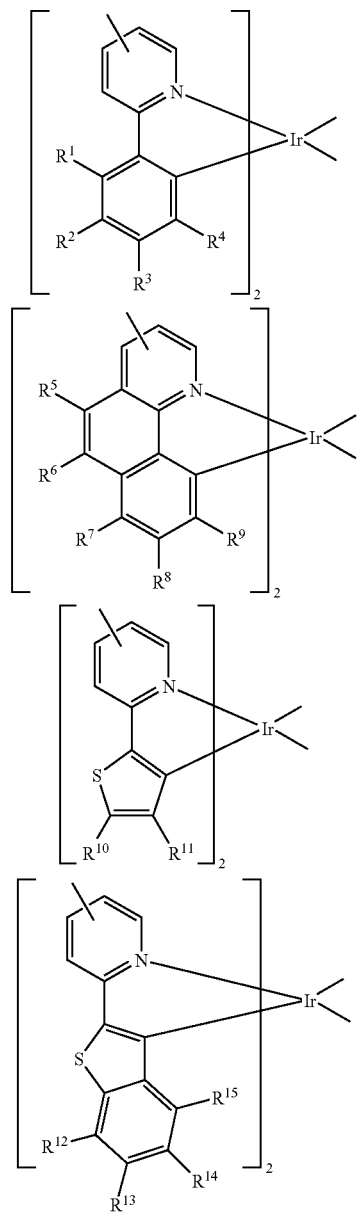

-continued
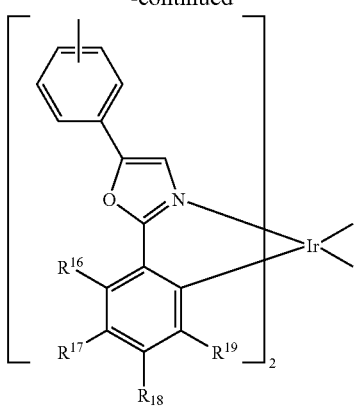
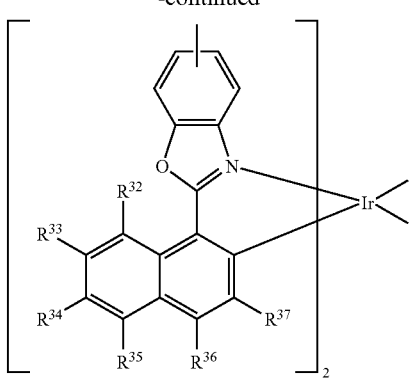
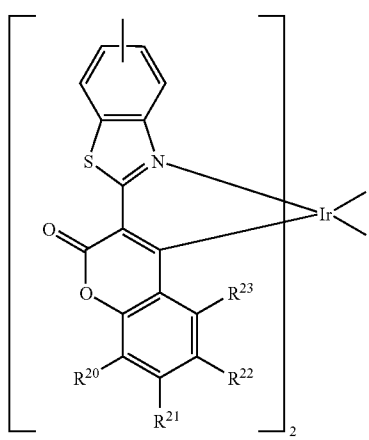
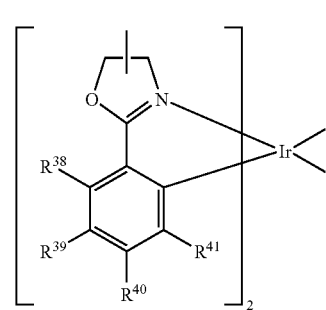
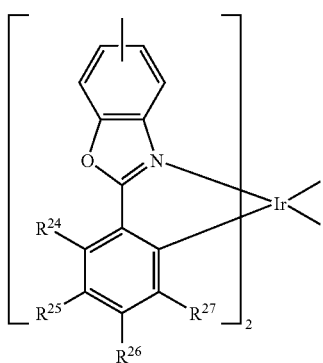
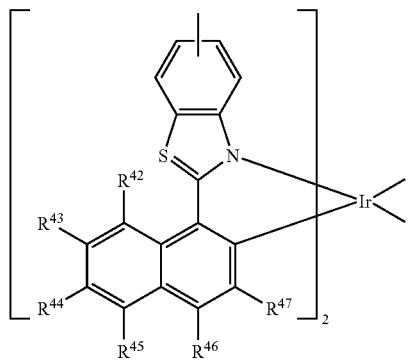
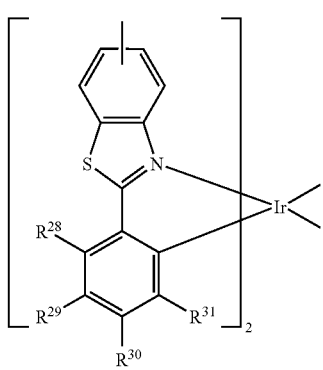
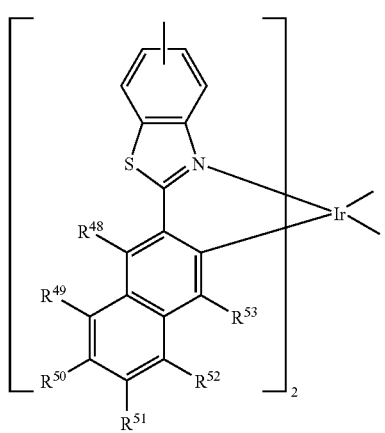

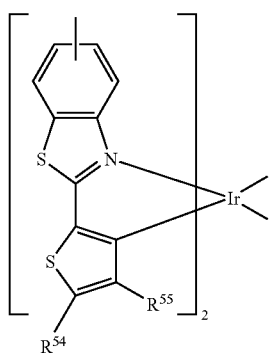
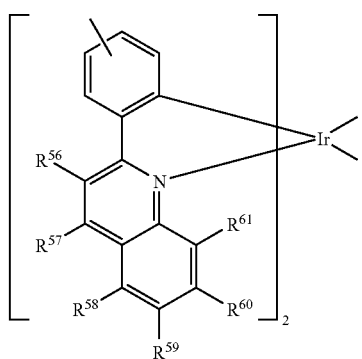
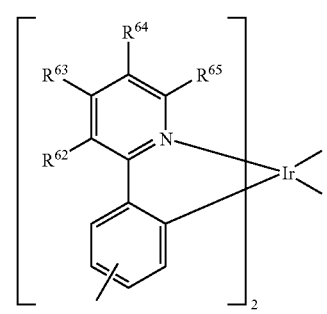
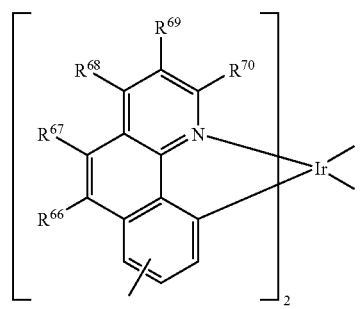
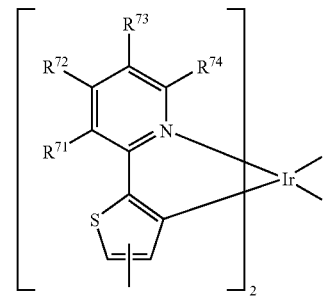
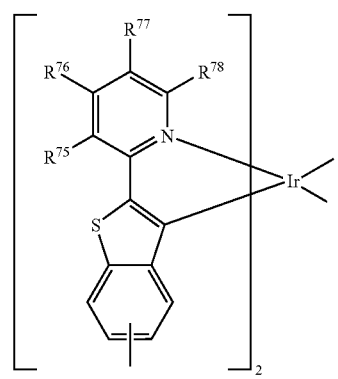
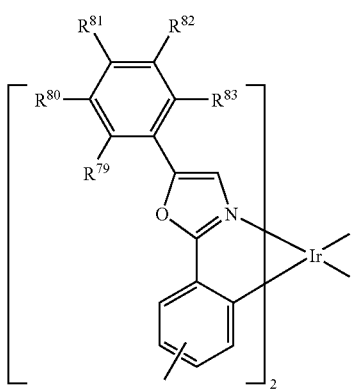
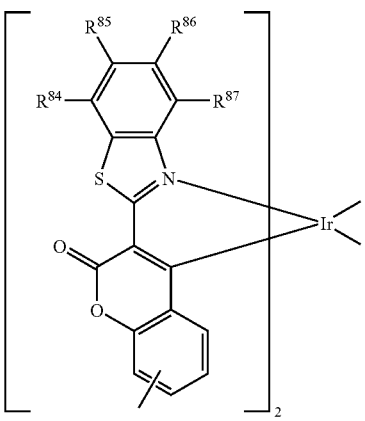
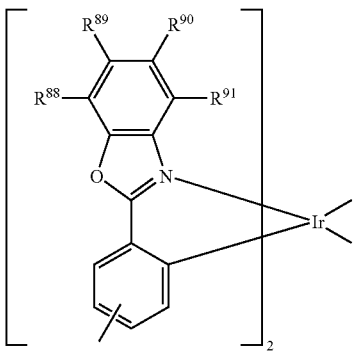

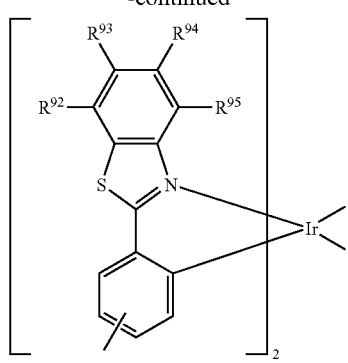

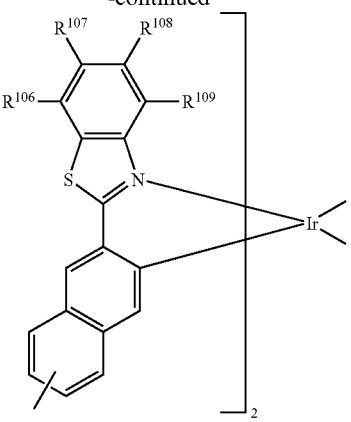

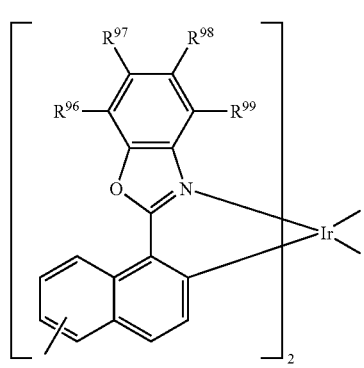

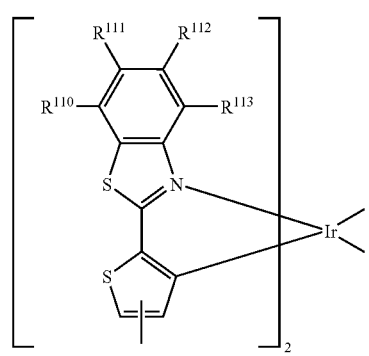

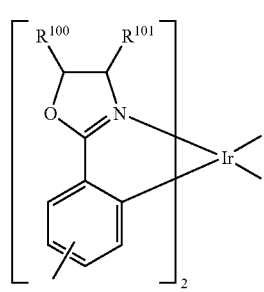

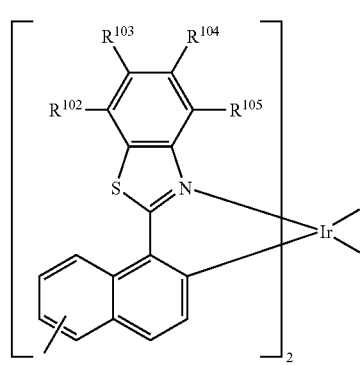

in which R' and R" are auxiliary ligands and $R^1 \sim R^{117}$ can be the same or different and they are independently selected from the group consisting of the following: hydrogen atom and electron-withdrawing group. The iridium complex containing (pentaphenyl)phenyl group provided by this embodiment can be used as the guest material in a phosphorescent device.

The electron-withdrawing group comprises one selected from the group consisting of the following: fluoro-group and trifluoro-methyl group. The R' and R" are each selected from one of the following:

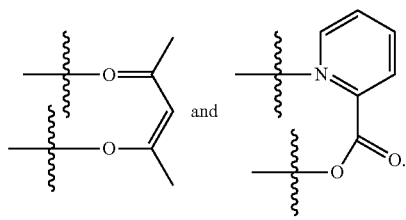
In a preferred example of this embodiment, the iridium complex containing (pentaphenyl)phenyl group comprises one selected from the group consisting of the following:
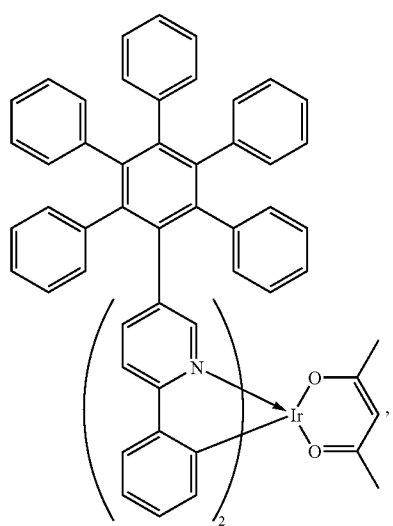
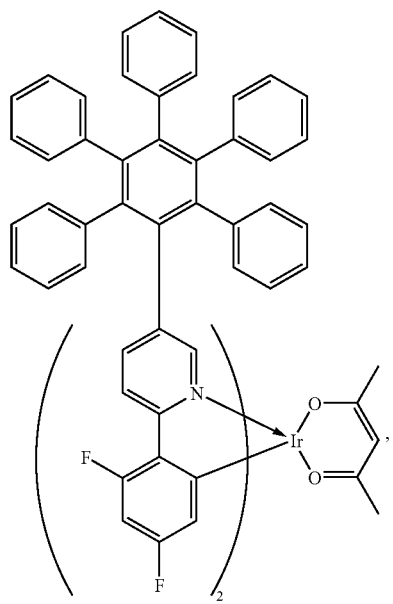
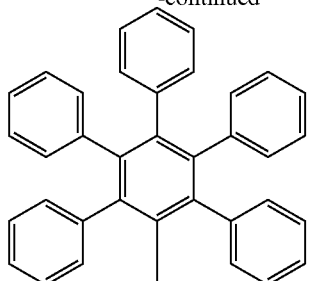
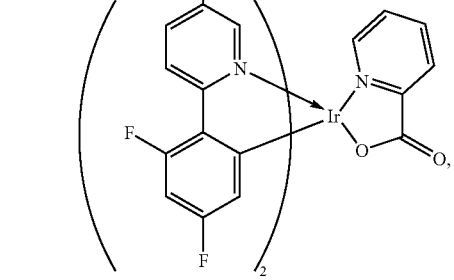
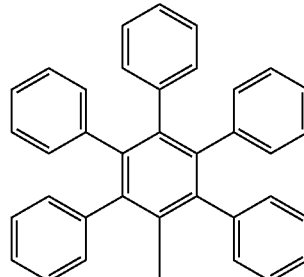
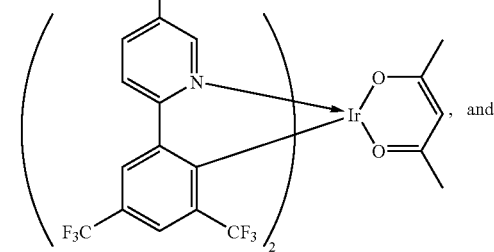
, and
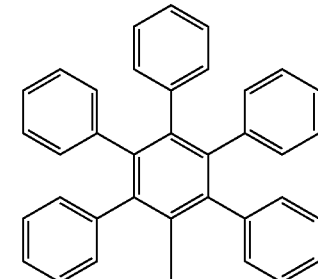
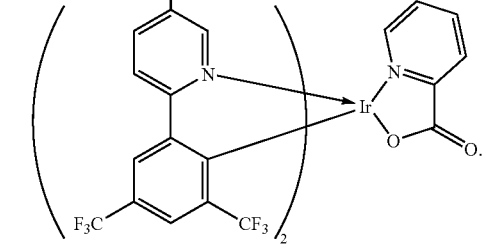

In a second embodiment of the present invention, a method for forming an iridium complex containing (pentaphenyl) phenyl group is provided. At first, a first reagent is provided, having the following general equation:

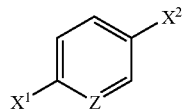

in which Z is a group VA element, $X^1$ and $X^2$ are independently selected from the group consisting of the following: chlorine (Cl), bromine (Br), and iodine (I), and $X^1$ is different from $X^2$. Next, a second reagent is provided, having the following general equation:

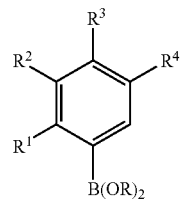

in which R is a hydrogen atom, alkyl group or aryl group, $R^1$, $R^2$, $R^3$, and $R^4$ can be the same or different, and $R^1$, $R^2$, $R^3$, and $R^4$ are independently selected from the group consisting of the following: hydrogen atom and electron-withdrawing group. Then, a Suzuki coupling reaction between the first reagent and the second reagent is carried out to form a first intermediate with the following structure:

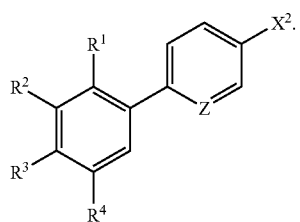

A Sonogashira coupling reaction between phenylacetylene and the first intermediate is carried out to form a second intermediate having the following general equation:

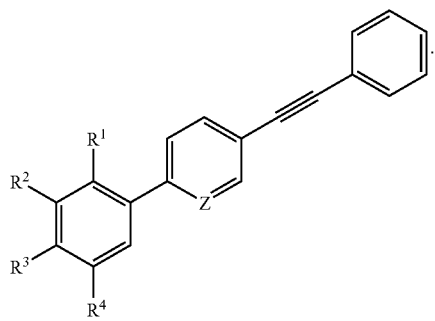

After Sonogashira coupling reaction is complete, a Diels-Alder reaction between tetraphenylcyclopentadienone (TPCDO) and the second intermediate is carried out to form a third intermediate having the following general equation:

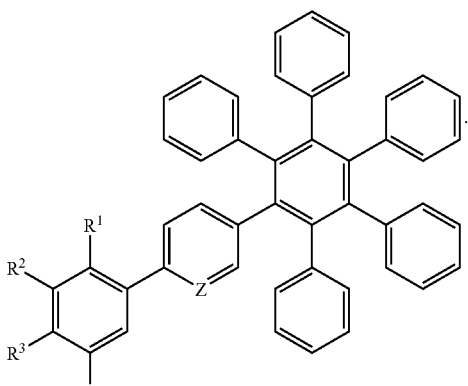

An addition reaction between iridium chloride and the third intermediate is carried out to form a halogen-bridged dimer iridium complex having the following general equation:

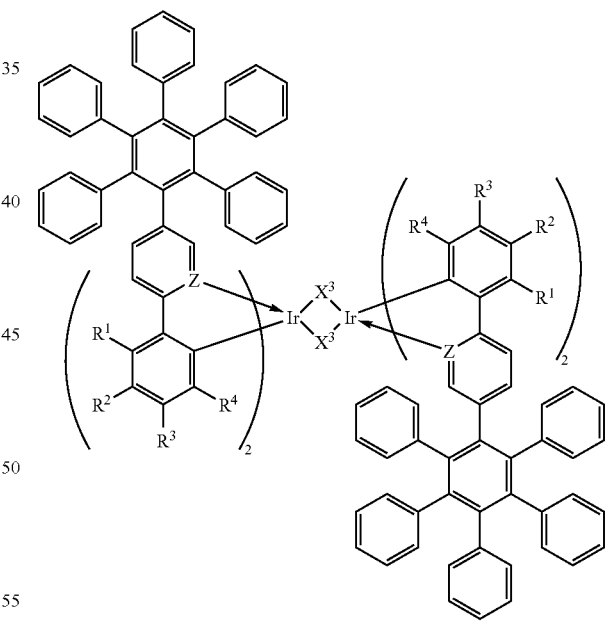

in which $X^3$ is selected from the group consisting of the following: chlorine (Cl), bromine (Br), and iodine (I). Finally, a substitution reaction between a chelating agent and the halogen-bridged dimer iridium complex is carried out to form the iridium complex containing a (pentaphenyl)phenyl ligand. The iridium complex containing a (pentaphenyl)phenyl ligand has the following general equation:

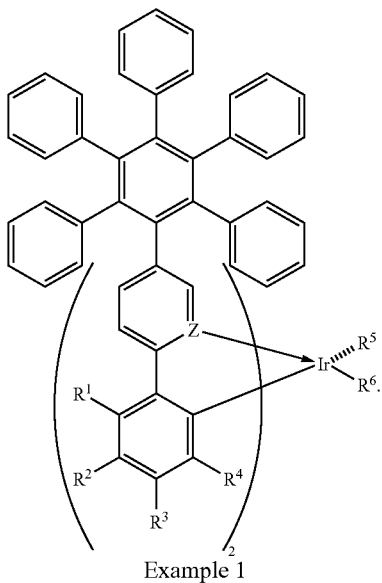

Example 1

Referring to scheme 1, 5-bromo-2-iodo-pyridine as a starting substance with selective reactivity reacts with Pd(PPh$_3$)$_4$ organic metallic catalyst. At first, the Suzuki coupling reaction between the starting substance and boric acid with different electron-withdrawing group is carried out. Then, the Sonogashira coupling reaction with phenylacetylene is carried out to substitute the bromine atom at the fifth position of the starting substance. Thus, this method can successfully obtain compounds 4~6 and have ideal yield.

Scheme 1

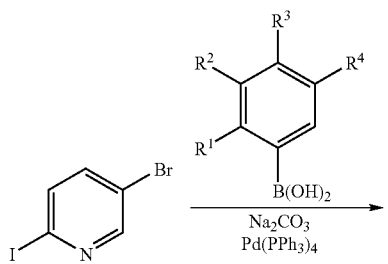

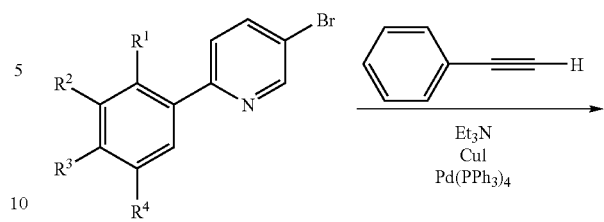

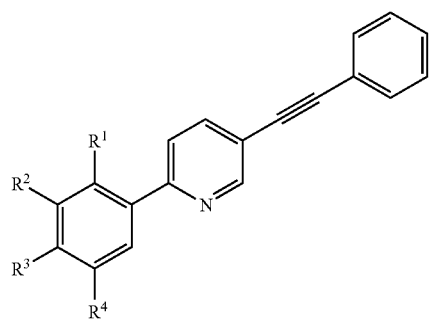

1 (R$^1$ = H, R$^2$ = H, R$^3$ = H, R$^4$ = H) 86%
2 (R$^1$ = F, R$^2$ = H, R$^3$ = F, R$^4$ = H) 89%
3 (R$^1$ = H, R$^2$ = CF$_3$, R$^3$ = H, R$^4$ = CF$_3$) 90%
4 (R$^1$ = H, R$^2$ = H, R$^3$ = H, R$^4$ = H) 83%
5 (R$^1$ = F, R$^2$ = H, R$^3$ = F, R$^4$ = H) 97%
6 (R$^1$ = H, R$^2$ = CF$_3$, R$^3$ = H, R$^4$ = CF$_3$) 97%

Referring to scheme 2, the Diels-Alder reaction between the compounds 4~6 and tetraphenylcyclopentadienone (TPCDO) is carried out. The reaction requires high temperature, about 260° C., and TPCDO is the reaction medium. Thus, no solvent is added. The reaction takes place about 3 hrs to obtain compounds 7~9 containing a (pentaphenyl)phenyl substituent.

Scheme 2

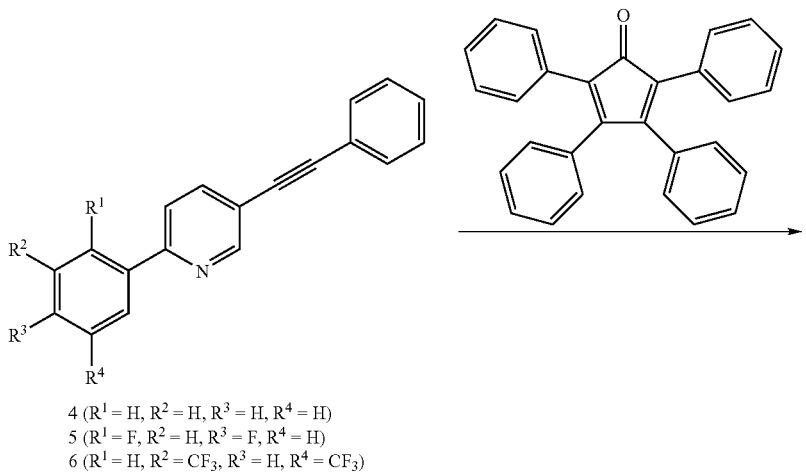

4 (R$^1$ = H, R$^2$ = H, R$^3$ = H, R$^4$ = H)
5 (R$^1$ = F, R$^2$ = H, R$^3$ = F, R$^4$ = H)
6 (R$^1$ = H, R$^2$ = CF$_3$, R$^3$ = H, R$^4$ = CF$_3$)

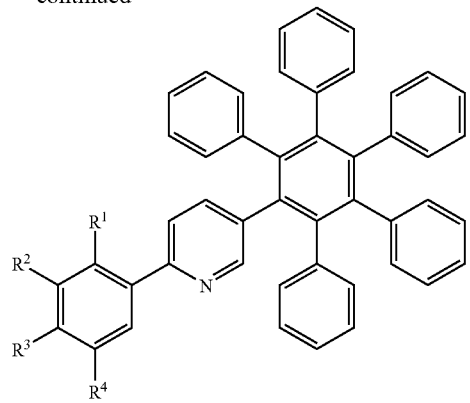

7 (R¹ = H, R² = H, R³ = H, R⁴ = H) 68%
8 (R¹ = F, R² = H, R³ = F, R⁴ = H) 97%
9 (R¹ = H, R² = CF₃, R³ = H, R⁴ = CF₃) 52%

Referring to scheme 3, in the synthesis of the iridium complex, the method reported by Nonoyama is used to synthesize a chlorine-bridged dimer iridium complex. 2-ethoxyethanol and deionized water with a ratio of 3:1 are used as the solvent. $IrCl_3 \cdot 3H_2O$ reacts with 2~2.5 equivalent of ligand. After filtered, powders of chlorine-bridged dimer iridium complexes 10~12 with pale yellow to yellow green color are obtained.

Scheme 3

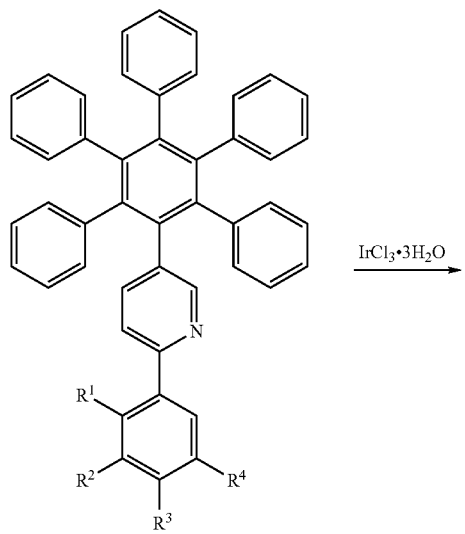

7 (R¹ = H, R² = H, R³ = H, R⁴ = H)
8 (R¹ = F, R² = H, R³ = F, R⁴ = H)
9 (R¹ = H, R² = CF₃, R³ = H, R⁴ = CF₃)

$\xrightarrow{IrCl_3 \cdot 3H_2O}$

-continued

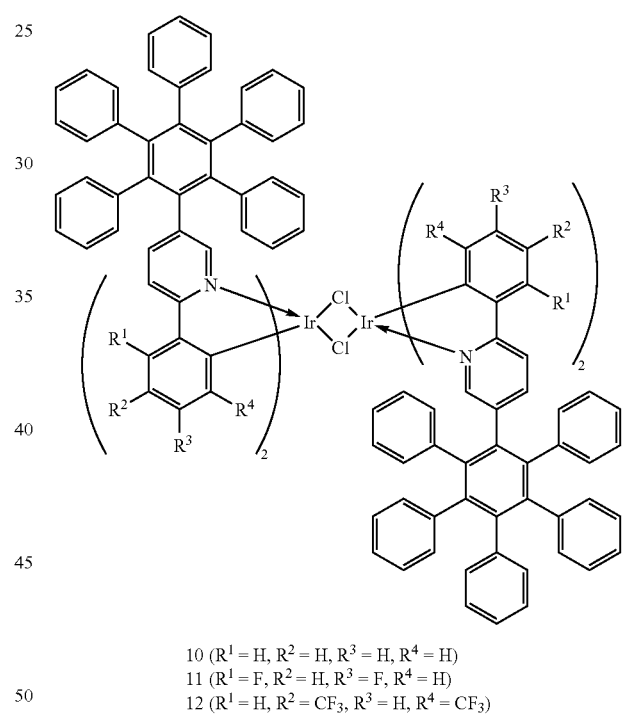

10 (R¹ = H, R² = H, R³ = H, R⁴ = H)
11 (R¹ = F, R² = H, R³ = F, R⁴ = H)
12 (R¹ = H, R² = CF₃, R³ = H, R⁴ = CF₃)

If the core of the complex, that is iridium, is tightly wrapped, the ligand can have intramolecular energy transfer and also prevent bare iridium from stacking with each other or forming excimer, that affects color purity. Therefore, the modification of the third ligand is proceeded. Referring to scheme 4, by using 2-ethoxyethanol as the solvent and sodium carbonate as the base, the reaction with various auxiliary ligands at 130° C. is carried out. After purified, the target iridium complexes 13~17 are obtained. The HOMO, energy level difference $E_g$, and LUMO of the complexes 13~17 are shown in Table 1.

TABLE 1
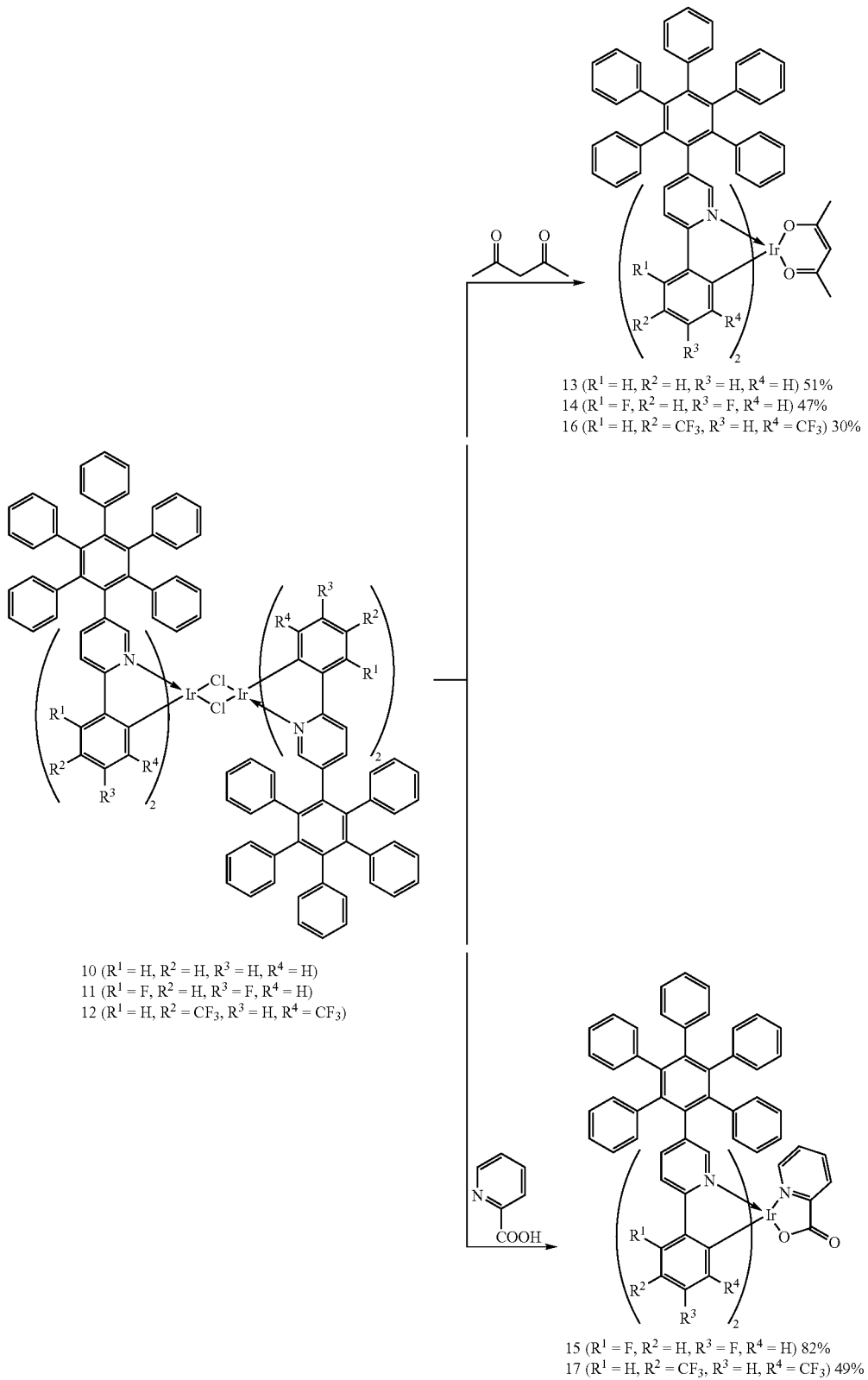

TABLE 1-continued

| Complexes | $E_{1/2}^{OX}$ (V) | HOMO (V) | λ (nm)[c] | Eg (V) | LUMO (V) |
|---|---|---|---|---|---|
| 13 Ir(ppy-6ph)$_2$(acac) | 0.861[a] | 5.116 | 486.5 | 2.550 | 2.566 |
| 14 Ir(F-ppy-6ph)$_2$(acac) | 1.165[a] | 5.420 | 458.0 | 2.709 | 2.711 |
| 15 Ir(F-ppy-6ph)$_2$(pic) | 1.378[a] | 5.633 | 441.5 | 2.811 | 2.822 |
| 16 Ir(CF$_3$-ppy-6ph)$_2$(acac) | 1.435[a] | 5.690 | 425.0 | 2.920 | 2.770 |
| 17 Ir(CF$_3$-ppy-6ph)$_2$(pic) | 1.613[b] | 5.903 | 413.5 | 3.001 | 2.902 |

[a]reversible redox potential relative to Cp$_2$Fe/Cp$_2$Fe$^+$, detected in methylenechloride, where $E_{1/2, Ferrocene}^{OX} = 0.545$ V
[b]reversible redox potential relative to Cp$_2$Fe/Cp$_2$Fe$^+$, detected in acetonitrile, where $E_{1/2, Ferrocene}^{OX} = 0.510$ V
[c]point of intersection between the edge of the maximum absorption wavelength in the UV-Vis spectrum and the horizontal line The spectra data of the compound 13 is as follows:
$^1$H NMR (400 MHz, CDCl$_3$): δ 7.92 (d, J=2.0 Hz, 2H), δ 7.29 (d, J=8.8 Hz, 2H), δ 7.16 (dd, J=2.0, 8.4 Hz, 2H), δ 6.98~6.70 (m, 52H), δ 6.66~6.64 (m, 2H), δ 6.61~6.59 (m, 2H), δ 5.69 (d, J=6.8 Hz, 2H), δ 4.95 (s, 1H), δ 1.70 (s, 6H); $^{13}$C NMR (100 MHz, CDCl$_3$): δ182.12, 164.79, 148.88, 147.16, 143.88, 140.74, 140.48, 140.28, 140.14, 139.99, 139.79, 139.73, 139.65, 139.12, 139.09, 138.77, 134.96, 134.07, 132.84, 130.96, 130.85, 130.79, 130.73, 130.70, 130.63, 130.60, 128.17, 127.35, 127.17, 126.60, 126.44, 126.28, 126.23, 126.19, 125.75, 125.14, 124.94, 124.90, 122.90, 119.84, 116.05, 101.55, 29.34; MS m/z FAB (NBA) 1414.3 (14), 1513.6 (4); HRMS (M$^+$) calcd for C$_{99}$H$_{71}$IrN$_2$O$_2$ 1512.5144. found 1512.5082 (M$^+$). Anal. calcd for C$_{99}$H$_{71}$IrN$_2$O$_2$: C, 78.60; H, 4.73; N, 1.85. found C, 78.74; H, 5.02; N, 1.98.

The spectra data of the compound 14 is as follows:
MS m/z FAB (NBA) 1585.8 (0.04), 1586.8 (0.02); HRMS (M$^+$) calcd for C$_{99}$H$_{67}$F$_4$IrN$_2$O$_2$ 1584.4767. found 1584.4712 (M$^+$). Anal. calcd for C$_{99}$H$_{67}$F$_4$IrN$_2$O$_2$: C, 75.03; H, 4.26; N, 1.77. found C, 75.07; H, 4.84; N, 1.53.

The spectra data of the compound 15 is as follows:
$^1$H NMR (400 MHz, CD$_2$Cl$_2$): δ 8.43 (d, J=8.0 Hz, 1H), δ 8.16 (d, J=1.6 Hz, 1H), δ 8.14~8.09 (m, 1H), δ 7.73~7.69 (m, 2H), δ 7.42~7.39 (m, 1H), δ 7.32 (d, J=5.2 Hz, 1H), δ 7.28 (dd, J=1.6, 8.4 Hz, 1H), δ 7.22 (dd, J=1.6, 8.4 Hz, 1H), δ 7.17~7.13 (m, 1H), δ 7.08 (t, J=7.6 Hz, 1H), δ 7.03~6.99 (m, 1H), δ 6.97~6.69 (m, 42H), δ 6.58 (d, J=2.0 Hz, 1H), δ 6.50 (d, J=7.2 Hz, 1H), δ 6.46 (d, J=7.6 Hz, 1H), δ 6.35~6.18 (m, 5H), δ 4.98 (dd, J=2.0, 7.8 Hz, 1H), δ 4.91 (dd, J=2.0, 7.8 Hz, 1H); $^{13}$C NMR (100 MHz, CD$_2$Cl$_2$): δ 171.41, 161.50, 160.60, 160.53, 159.03, 152.72, 151.52, 150.31, 149.36, 149.21, 148.59, 141.50, 141.32, 140.85, 140.74, 140.65, 140.54, 140.38, 140.26, 140.23, 140.12, 140.05, 139.97, 139.86, 139.71, 139.51, 139.30, 139.25, 139.03, 138.11, 135.90, 135.65, 134.47, 134.37, 131.43, 131.35, 131.32, 131.24, 131.20, 131.09, 131.04, 130.99, 130.89, 130.75, 130.68, 130.62, 130.16, 128.45, 128.37, 127.78, 127.59, 127.04, 126.97, 126.90, 126.80, 126.62, 126.58, 126.48, 126.43, 126.39, 126.11, 125.44, 125.34, 125.17, 121.25, 121.05, 120.74, 120.56, 115.34, 115.19, 114.59, 97.97, 97.71, 97.36; MS m/z FAB (NBA) 1486.3 (100), 1608.9 (48); HRMS (M$^+$) calcd for C$_{100}$H$_{64}$F$_4$IrN$_3$O$_2$ 1607.4563. found 1607.4633 (M$^+$).

The spectra data of the compound 16 is as follows:
$^1$H NMR (400 MHz, CDCl$_3$): δ 7.74 (s, 2H), δ 7.62 (s, 2H), δ 7.40~7.33 (m, 6H), δ 7.29 (s, 2H), δ 6.97~6.60 (m, 50H), δ 4.68 (s, 1H), δ 1.60 (s, 6H); $^{13}$C NMR (100 MHz, CDCl$_3$): δ 183.05, 162.66, 150.31, 150.25, 141.32, 141.26, 141.02, 140.68, 140.65, 139.96, 139.94, 139.91, 139.74, 139.45, 138.54, 136.41, 136.11, 134.03, 133.70, 132.02, 131.21, 131.05, 130.95, 130.90, 130.83, 130.76, 130.64, 130.52, 127.33, 127.01, 126.84, 126.52, 126.40, 126.36, 126.32, 126.14, 125.81, 125.66, 125.20, 125.14, 123.13, 123.15, 122.83, 121.70, 121.29, 116.73, 101.83, 29.46; MS m/z FAB (NBA) 1686.7 (100), 1786.1 (34); HRMS (M$^+$) calcd for C$_{103}$H$_{67}$F$_{12}$IrN$_2$O$_2$ 1784.4640. found 1784.4620 (M$^+$). Anal. calcd for C$_{103}$H$_{67}$F$_{12}$IrN$_2$O$_2$: C, 69.31; H, 3.78; N, 1.57. found C, 69.05; H, 4.03; N, 1.55.

The spectra data of the compound 17 is as follows:
$^1$H NMR (400 MHz, CDCl$_3$): δ 8.36 (d, J=8.0 Hz, 1H), δ 8.13~8.08 (m, 2H), δ 7.77 (s, 2H), δ 7.45~7.40 (m, 3H), δ 7.35~7.26 (m, 4H), δ 7.20 (dd, J=2.0, 8.6 Hz, 1H), δ 7.13 (s, 1H), δ 7.00~6.92 (m, 5H), δ 6.88~6.56 (m, 39H), δ 6.50~6.46 (m, 2H), δ 6.36 (d, J=7.6 Hz, 1H), δ 6.19 (d, J=6 Hz, 1H), δ 6.00 (d, J=5.6 Hz, 2H); $^{13}$C NMR (100 MHz, CDCl$_3$): δ 170.91, 162.96, 161.63, 151.61, 150.05, 149.81, 148.99, 147.66, 141.48, 141.34, 141.00, 140.75, 140.69, 140.36, 140.24, 140.06, 140.00, 139.82, 139.80, 139.71, 139.68, 139.48, 138.56, 138.43, 138.37, 138.21, 136.18, 135.71, 135.24, 133.38, 133.11, 131.64, 131.10, 131.02, 130.93, 130.84, 130.80, 130.71, 130.34, 130.17, 129.89, 128.80, 128.04, 127.62, 127.09, 126.55, 126.51, 126.46, 126.33, 126.24, 126.07, 125.28, 125.17, 125.10, 125.01, 122.88, 121.96, 117.83, 117.11; MS m/z FAB (NBA) 1686.2 (100), 1808.7 (44); HRMS (M$^+$) calcd for C$_{104}$H$_{64}$F$_{12}$IrN$_3$O$_2$ 1807.4436. found 1807.4353 (M$^+$).

Example 2

Generally, vacuum evaporation is utilized to fabricate the OLED devices. In the vacuum evaporation method, compounds are evaporated under vacuum and deposited on the ITO glass. However, the compounds have to sustain high temperature like 300~400° C. without decomposition or transformation. If the compounds decompose during the evaporation process, the decomposed compounds will contaminate the device to jeopardize the performance of the device. In the present invention, although the device is made by spin coating without direct heating compounds, the external current applied on these compounds during operating or testing generates heat and transfers heat to these compounds. Therefore, the materials used in the OLED devices require thermal stability. If the thermal decomposition temperature (T$_d$) of the material is too low, its application will be limited.

On the other hand, the glass transition temperature (T$_g$) of the material also affects the lifetime, efficiency, and chromatic aberration of the device. Thus, if the T$_g$ of the material is too low, the external heat source will soften the material or cause molecules to crystallize so as to have the diffusion problem in the interface, during the fabricating or testing process. The thermal characteristics of the iridium complexes 13~17 in the example 1 are shown in Table 2.

TABLE 2

| Compound | Molecular weight | $T_d$ | $T_g$ |
|---|---|---|---|
| 13 | 1512.51 | 423 | 222 |
| 14 | 1584.48 | 399 | 221 |
| 15 | 1607.46 | 459 | — |
| 16 | 1784.46 | 411 | 219 |
| 17 | 1807.44 | 470 | 245 |

Example 3 Fabrication and characteristics of the OLED device where the iridium complexes 13~17 are doped in PVK.

The compound 14 is only slightly dissolved in dichlorobenzene and has terrible film formation property by spin coating its dichlorobenzene solution. The efficiency of the compound 14 is low. Therefore, the device characteristics are discussed only for those made with the iridium complexes 13, 15, 16, and 17.

The iridium complexes 13 and 15-17 are doped in poly (vinylcarbazole) [PVK, average MW 90000] and PVK is the host material. PVK, one of the carbazole derivatives, has good hole transport capability. The electron from cathode can stay on the iridium complex to wait for recombination with hole so as to emit light.

Figure 2:
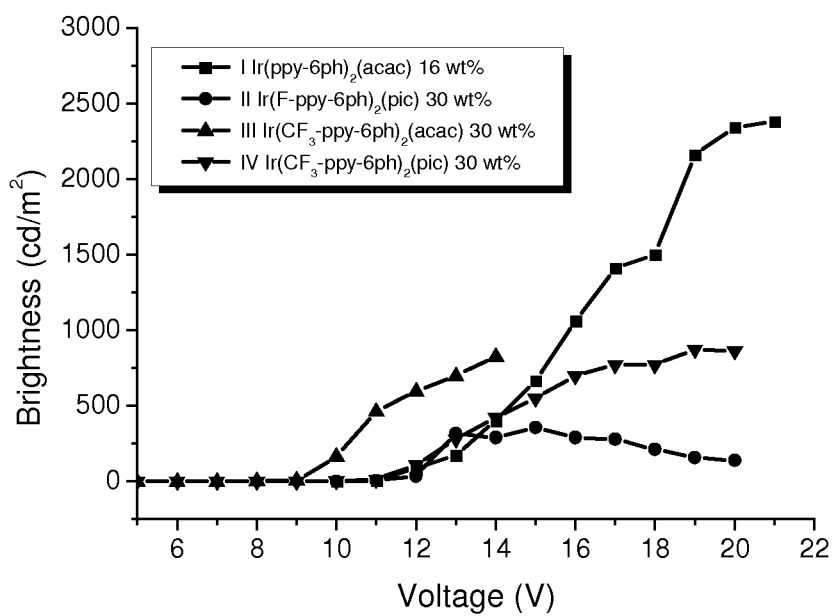
FIG. 2 shows brightness-voltage curves for the devices I, II, III, and IV according to the example 3 of the present invention.
Figure 3:
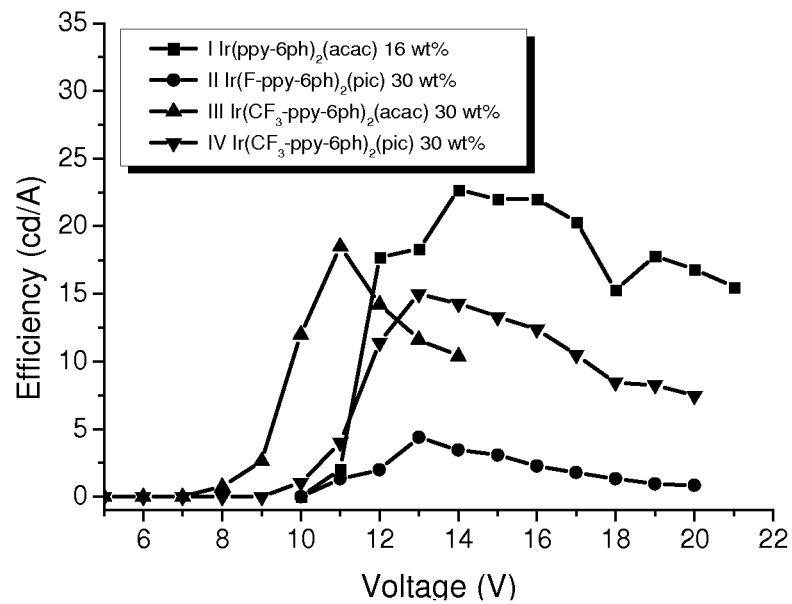
FIG. 3 shows efficiency-voltage curves for the devices I, II, III, and IV according to the example 3 of the present invention.
Figure 4:
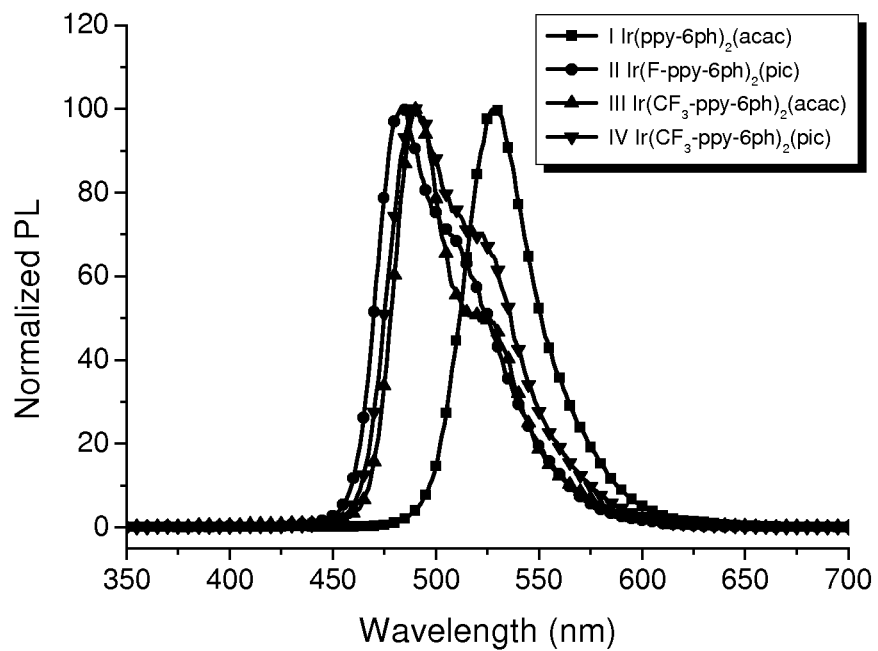
FIG. 4 shows electroluminescence spectra for the devices I, II, III, and IV according to the example 3 of the present invention.
Figure 5:
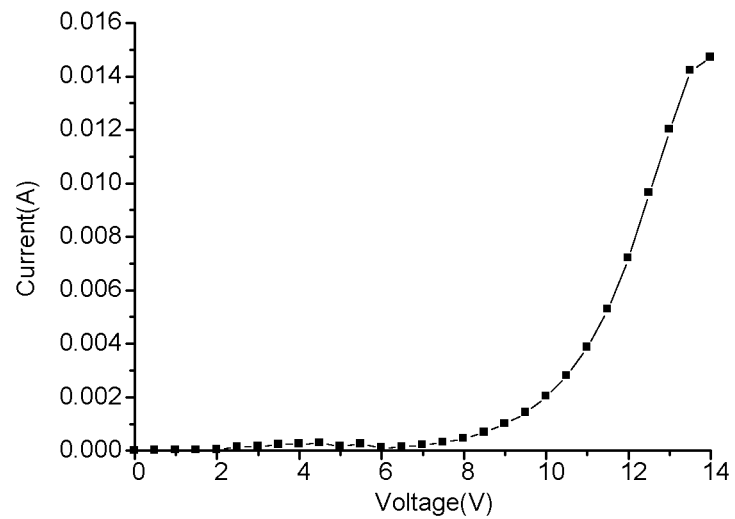
FIG. 5 shows a voltage-current curve for the device V according to the example 6 of the present invention.
Figure 6:
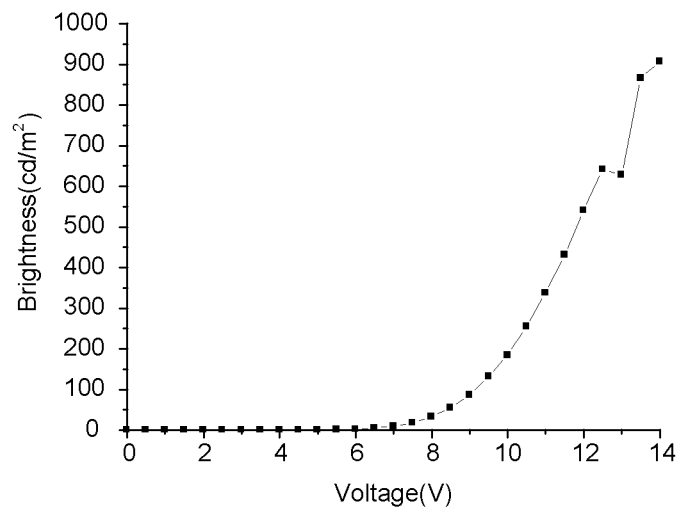
FIG. 6 shows a brightness-voltage curve for the device V according to the example 6 of the present invention.
Figure 7:
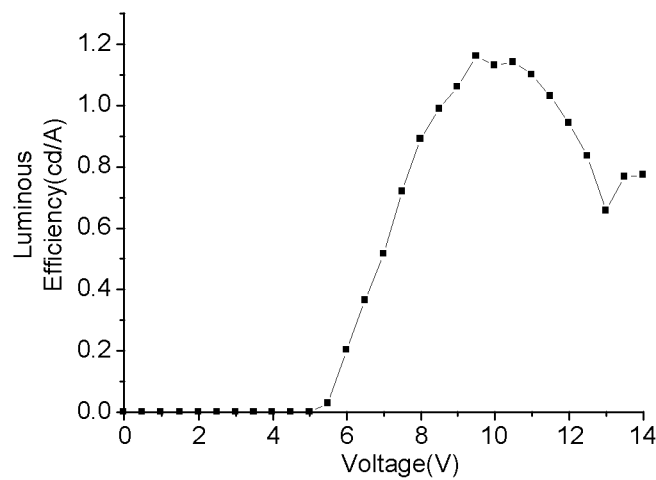
FIG. 7 shows an efficiency-voltage curve for the device V according to the example 6 of the present invention.
Figure 8:
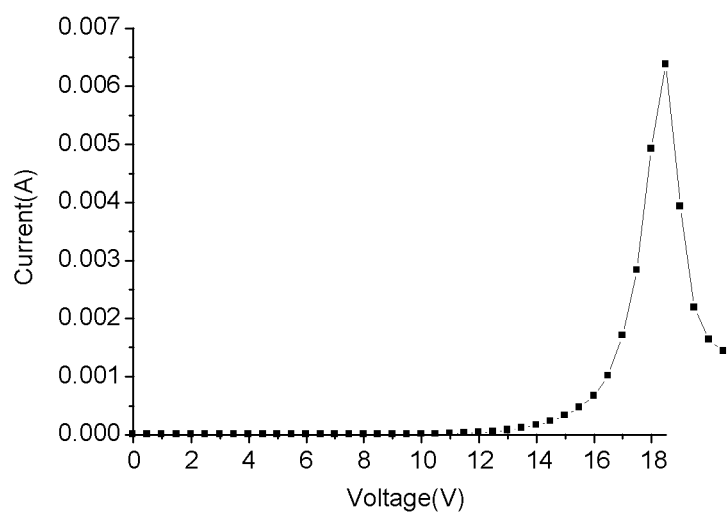
FIG. 8 shows a voltage-current curve for the device VI according to the example 6 of the present invention.
Figure 9:
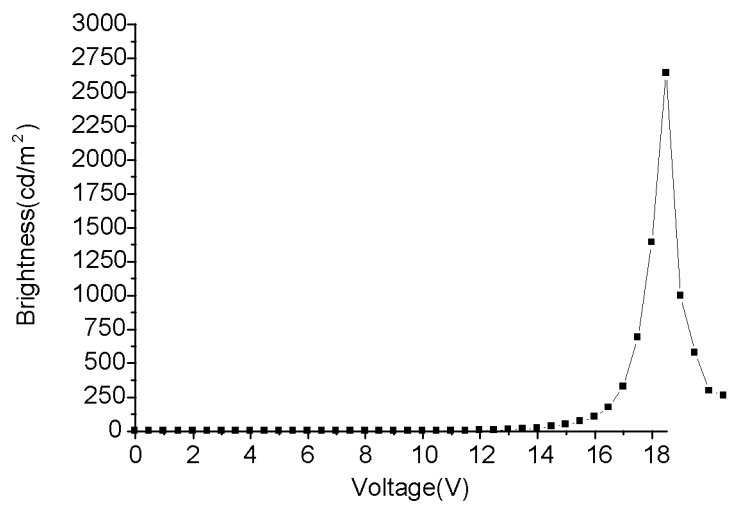
FIG. 9 shows a brightness-voltage curve for the device VI according to the example 6 of the present invention.
Figure 10:
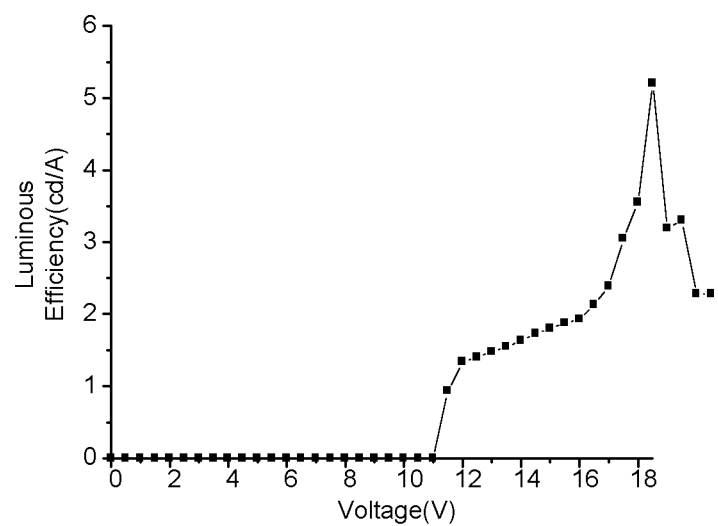
FIG. 10 shows an efficiency-voltage curve for the device VI according to the example 6 of the present invention.
Figure 11:
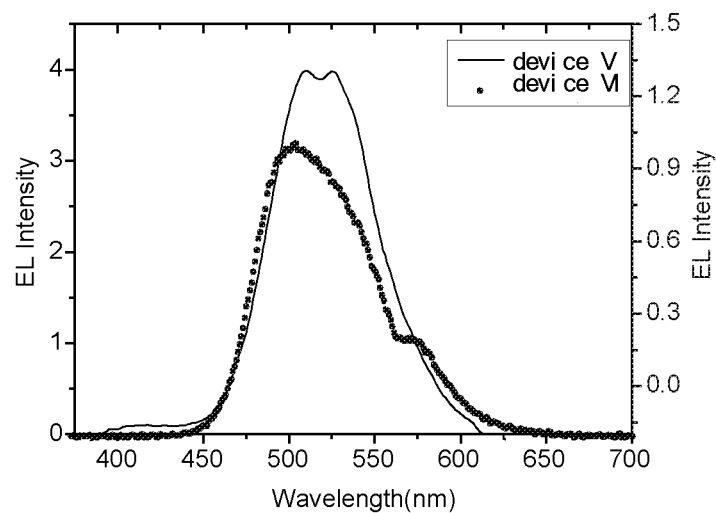
FIG. 11 shows electroluminescence spectra for the devices V and VI according to the example 6 of the present invention.

The fabricating processes of the device are described in the following. (1) For the hole injection layer, poly(3,4-ethylene-dioxythiophene)-poly(styrene)sulfonic acid (hereinafter referred to as "[PEDOT/PSS]") is spin coated with a thickness of 50 nm. (2) For the light emitting layer, 100 mg of the host material, PVK, 40 mg of the electron transport material, 2-(4-biphenylyl-5-(4-tertbutylphenyl)-1,2,3-oxadiazole (PBD), and the iridium complexes 13 and 15-17 with different doping ratios are added in 8 ml of the chloroform solution and the solution is spin coated and baked on the hole injection layer. (3) For the cathode, traditionally the metal or metal alloy with low work function, such as active metals like Li, Mg, Ca, is used to have electrons from the cathode injected into the electron transport layer. The cathode is formed by thermal evaporation. In addition, an electron injection layer can be provided between the cathode and the electron transport layer to reduce the energy barrier between the cathode and the electron transport layer so as to lower the driving voltage. The common material for the electron injection layer is very thin metal halide or oxide, such as LiF, MgO, or $Li_2O$. The complete OLED device has a structure of ITO/PEDOT/ 13, 15-17-PBD-PVK/Mg/Ag (hereinafter referred to as "device I, II, III, and IV", respectively). The content of the doped iridium complexes 13 and 15-17 ranges about 15 wt %~40 wt %. The result is shown in FIGS. 1~3. The maximum brightness for the device I, II, III, and IV is 2380, 355, 824, and 871 $cd/m^2$, respectively, and the maximum efficiency is 22.7, 4.37, 18.5, and 15 cd/A, respectively. Besides, the electroluminescent spectra for the device I, II, III, and IV are shown in FIG. 4. Referring to FIG. 5, there is no red shift for the device with an increased doping ratio. Thus, the core metal of the compounds 13 and 15-17 is wrapped tightly. Therefore, T-T annihilation due to the higher doping ratio in fabricating does not occur. Besides, the luminance intensity is generally proportioned to the content of iridium. According to the present invention, the brightness can be increased by the increase of the doping ratio of the iridium complex.

A third embodiment of the present invention discloses a compound with a 9-[(pentaphenyl)phenyl]carbazole structure, having the following general equation:

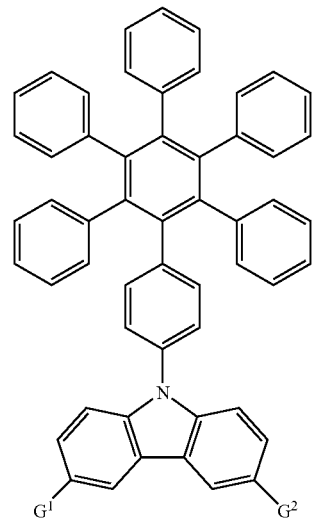

in which $G^1$ and $G^2$ can be the same or different and $G^1$ and $G^2$ are independently selected from the group consisting of the following: hydrogen atom, carboxyl group, hydroxyl group, amino group, double bond group or triple bond group, halogen atom,

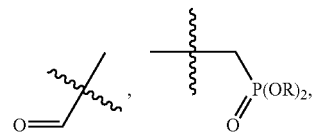

—$B(OR)_2$,

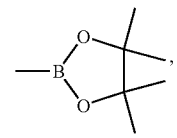

and —$Ar-G^3$, where R is a hydrogen atom, alkyl group, or aryl group, Ar is an aryl group, $G^3$ is a hydrogen atom, carboxyl group, hydroxyl group, amino group, double bond group or triple bond group. In addition, the compound with a 9-[(pentaphenyl)phenyl]carbazole structure provided by the invention can be applied in an organic solar cell device or as a hole injection material, hole transport material, emitting material or host material in an organic electroluminescence device and/or phosphorescence device.

The compound with a 9-[(pentaphenyl)phenyl]carbazole structure provided by this embodiment can be used to form a polymer derived from a 9-[(pentaphenyl)phenyl]carbazole structure by the reaction between the compound with a 9-[(pentaphenyl)phenyl]carbazole structure and at least one reactive monomer. The reactive monomer is selected from the group consisting of the following:

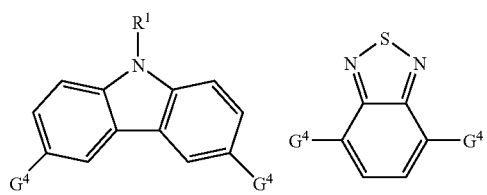

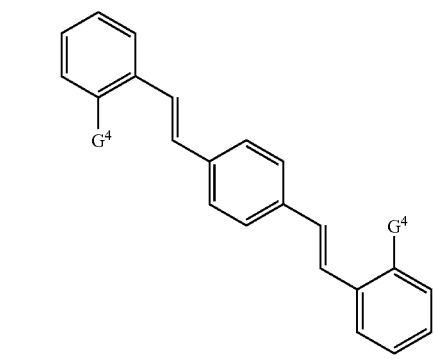

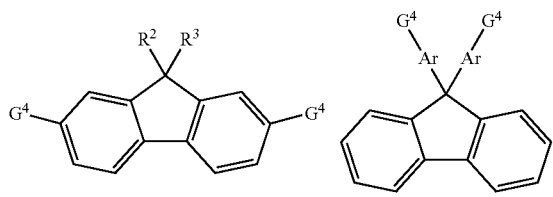

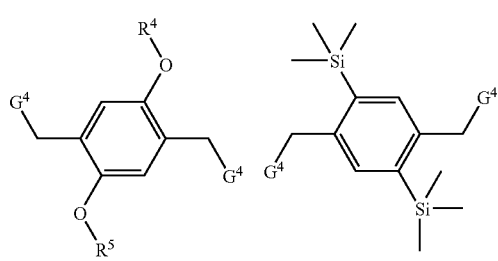

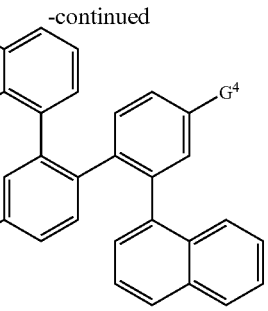

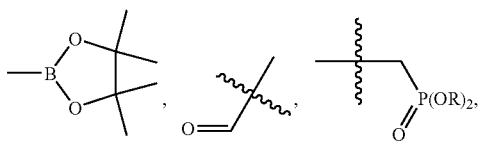

in which $R^1$, $R^2$, $R^3$, $R^4$, and $R^5$ are independently selected from the group consisting of the following: alkyl group and aryl group, $G^4$ is a halogen atom, —$B(OR)_2$, carboxyl group, hydroxyl group, amino group, double bond group or triple bond group, where R is a hydrogen atom, alkyl group, or aryl group. The polymer derived from a 9-[(pentaphenyl)phenyl]carbazole structure can be applied in an organic solar cell device or as a hole injection material, hole transport material, emitting material or host material in an organic electroluminescence device and/or phosphorescence device.

Example 4

This example provides seven polymers derived from a 9-[(pentaphenyl)phenyl]carbazole structure, as shown in the following P1-P7, and a comparison polymer P8. The synthesis of the polymers P1, P2, and P4-P8 utilizes Suzuki coupling reaction. At first, borate or boric acid compound monomer and brominated monomer are dissolved in THF (as the solvent), $Pd(PPh_3)_4$ is the catalyst, $P(t-Bu)_3$ is the ligand, $K_3PO_4$ is also added, and reflux reaction is carried out for 40 hrs under the reaction temperature of 70° C. Next, triphenylammonium bromide as a terminal group is added and the reaction proceeds for one additional day and then stops. Finally, chloroform is used to extract the crude polymer product. Toluene is used as the elute and the chromatographic column is used to remove salts and heavy metal catalyst. The product is treated by vacuum concentration and then reprecipitated in methanol. Thus, the purified polymer is obtained. The molecular weights and distribution of the polymers P1-P8 are shown in Table 3. Their HOMO and LUMO energy levels are shown in Table 4.

TABLE 3
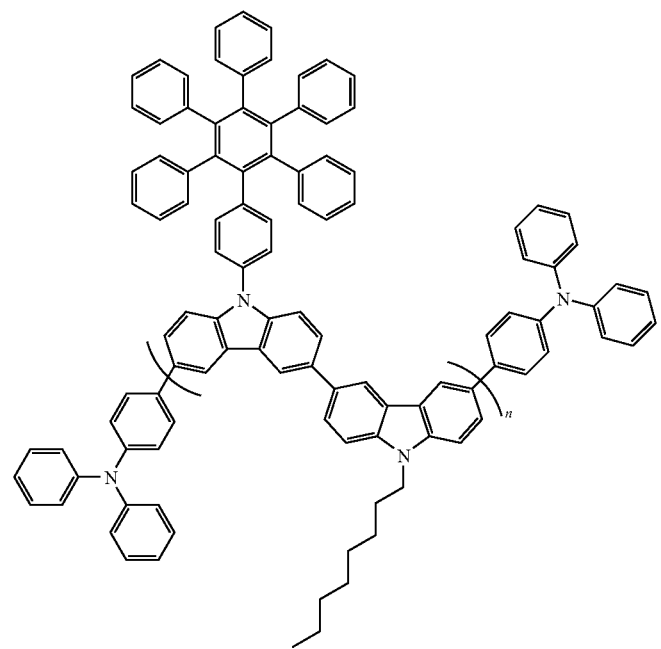
P1
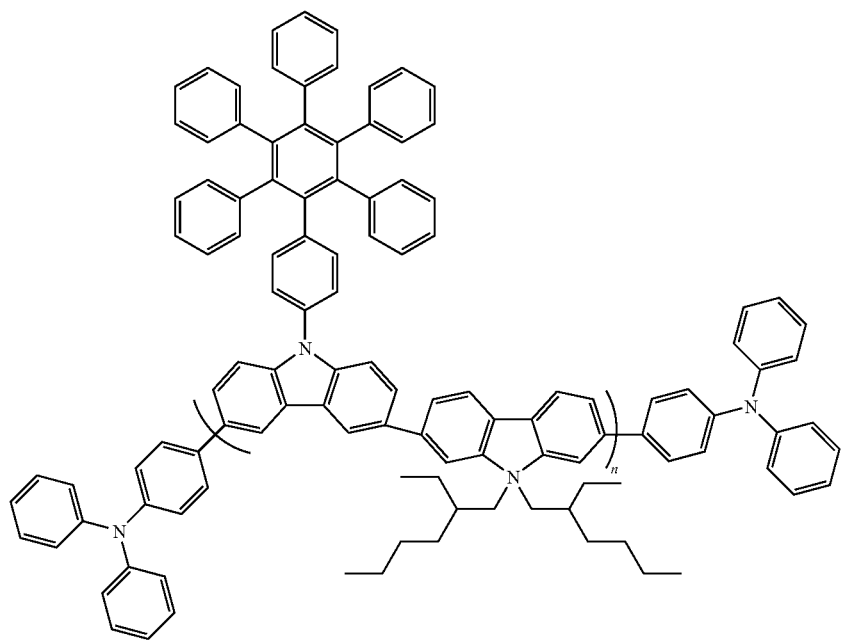
P2

TABLE 3-continued
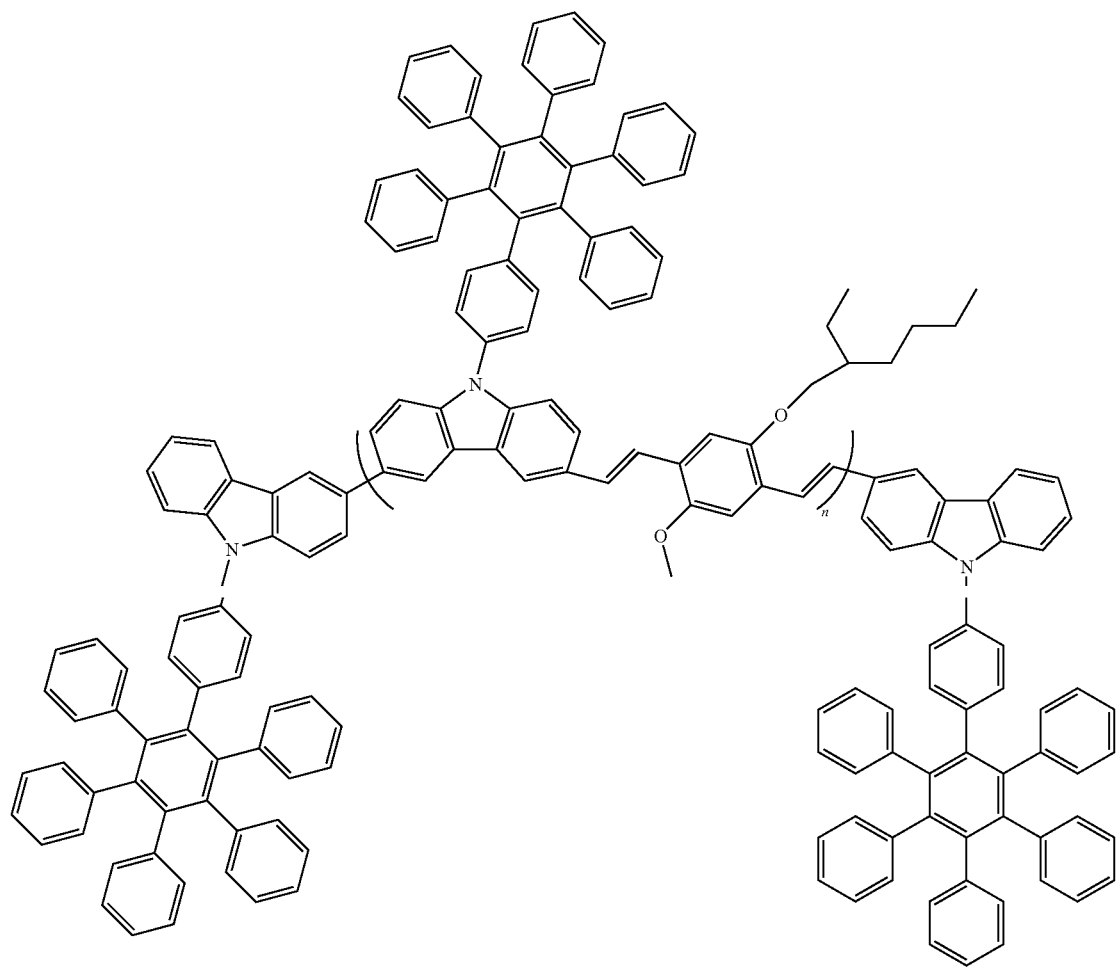
P3
P4
(x:y:z = 48:50:2)

TABLE 3-continued
P5
(x:y:z = 48:50:2)
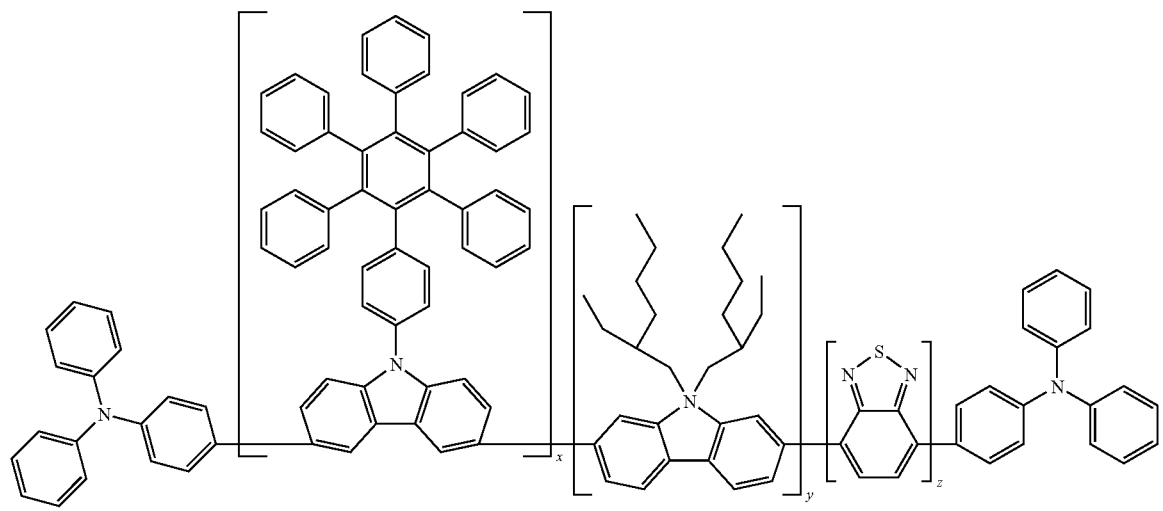
P6
(x:y:z = 48:50:2)
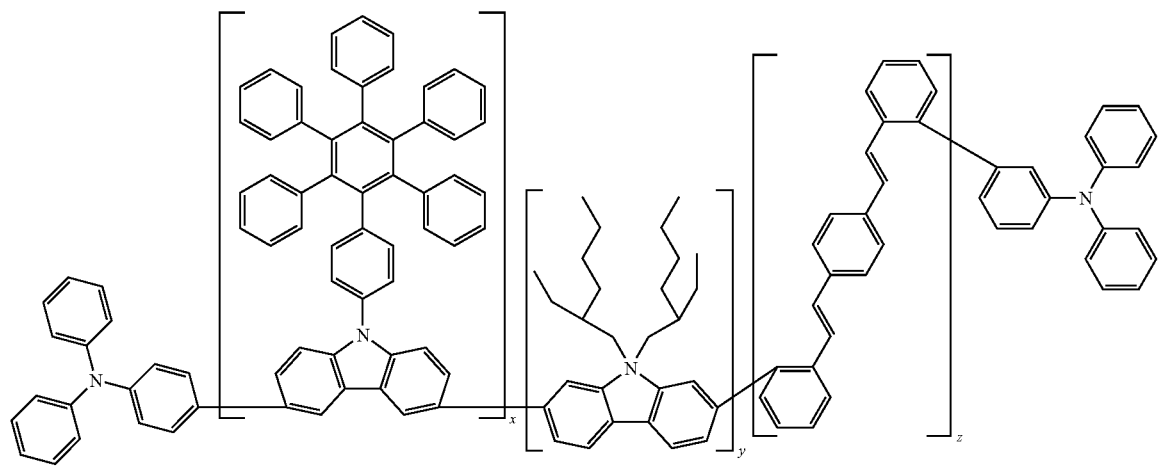
P7
(x:y:z = 48:50:2)

TABLE 3-continued

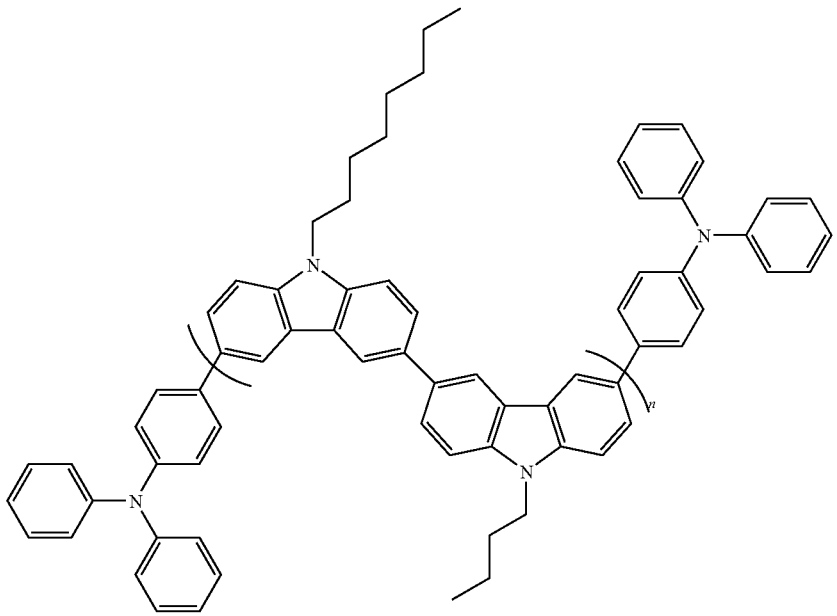

|    | Mn    | Mw    | PDI  |
|----|-------|-------|------|
| P1 | 4400  | 5500  | 1.25 |
| P2 | 14200 | 21000 | 1.48 |
| P3 | 24000 | 35500 | 1.48 |
| P4 | 16100 | 21200 | 1.33 |
| P5 | 12200 | 18000 | 1.5  |
| P6 | 16100 | 21600 | 1.35 |
| P7 | 15200 | 21100 | 1.39 |
| P8 | 6900  | 9100  | 1.32 |

TABLE 4

|    | Oxidation potential (V) | Energy level difference (eV) | HOMO | LUMO |
|----|------|------|------|------|
| P1 | 0.87 | 3.16 | 5.13 | 1.97 |
| P2 | 1.08 | 3.08 | 5.34 | 2.26 |
| P3 | 0.68 | 2.49 | 4.94 | 2.45 |
| P4 | 0.85 | 3.2  | 5.11 | 1.91 |
| P5 | 0.81 | 3.16 | 5.07 | 1.91 |
| P6 | 1.08 | 3.09 | 5.34 | 2.25 |
| P7 | 1.2  | 3.08 | 5.46 | 2.38 |
| P8 | 0.8  | 3.2  | 5.06 | 1.86 |

The effect of the thermal stability to the performance of the device can be explained in the following two parts. The first part is about the stability of the fabricating process at the early stage. The film of the polymer material is formed by spin coating without the requirement of vacuum evaporation, like that for the small molecule material, but the electrode is formed by thermal evaporation of metal. Thus, although the film of the compound is not heated directly, the temperature is still high as the metal is deposited on the polymer film. Therefore, if the thermal decomposition temperature is too low, decomposition occurs during evaporation. The second part is about the stability of the fabricating process at the later stage. The external voltage is continuously applied on the device during operation to generate heat and besides the heat of the operating environment is absorbed by the polymer in the device. Thus, if the glass transition temperature ($T_g$) is low, the organic material softens and the efficiency of the device is thereby affected.

Before fabricating the device, thermogravimetry analysis (TGA) is used to measure the thermal decomposition temperature ($T_d$) of the compound and differential scanning calorimetry (DSC) is used to measure the glass transition temperature ($T_g$) of the compound so as to realize the thermal property of the material. The glass transition temperatures ($T_g$) and the thermal decomposition temperatures ($T_d$) of the polymers P1-P8 are shown in Table 5. The thermal decomposition temperatures ($T_d$) are all higher than 400° C. They all have good thermal stability. The glass transition temperatures ($T_g$) are all between 100~120° C. and the $T_g$'s of P1-P7 are higher than that of P8, without (pentaphenyl)phenyl group on the backbone. It is suspected that the steric effect of (pentaphenyl)phenyl group is so large that the rotational degree of freedom is decreased and thus $T_g$ is increased.

TABLE 5

|    | Thermal decomposition temperature (Td) | Glass transition temperature (Tg) |
|----|--------|--------|
| P1 | 436° C. | 118° C. |
| P2 | 415° C. | 99° C.  |
| P3 | 432° C. | 112° C. |
| P4 | 430° C. | 118° C. |
| P5 | 421° C. | 113° C. |
| P6 | 415° C. | 109° C. |
| P7 | 418° C. | 91° C.  |
| P8 | 440° C. | 83° C.  |

Example 5

Scheme 5 shows the synthesis process flow of P3. Horner-Wadsworth-Emmons reaction (HWE reaction) is utilized to polymerize P3. Under alkaline condition, the compound 14 reacts with the compound 15 to form carbon-carbon double bond so as to polymerize P3. It is predicted that the polymer formed by HWE reaction has higher molecular weight than that formed by Suzuki coupling reaction.

Example 6

P6 is used to fabricate the OLED devices V and VI, having the structures of ITO/PEDOT:PSS/P6/LiF/Al and ITO/PEDOT:PSS/P6-PBD-Ir(ppy)$_3$/LiF/Al where P6:PBD:Ir(ppy)$_3$ in weight ratio is 100:40:8(THF). Referring to FIGS. 5~11, the device V with pure P6 emits green light and has a maximum brightness of 910 cd/m$^2$. The performance of the device is fairly good without mixing any electron or hole transport material. The device VI mixed with iridium phosphorescent Scheme 5

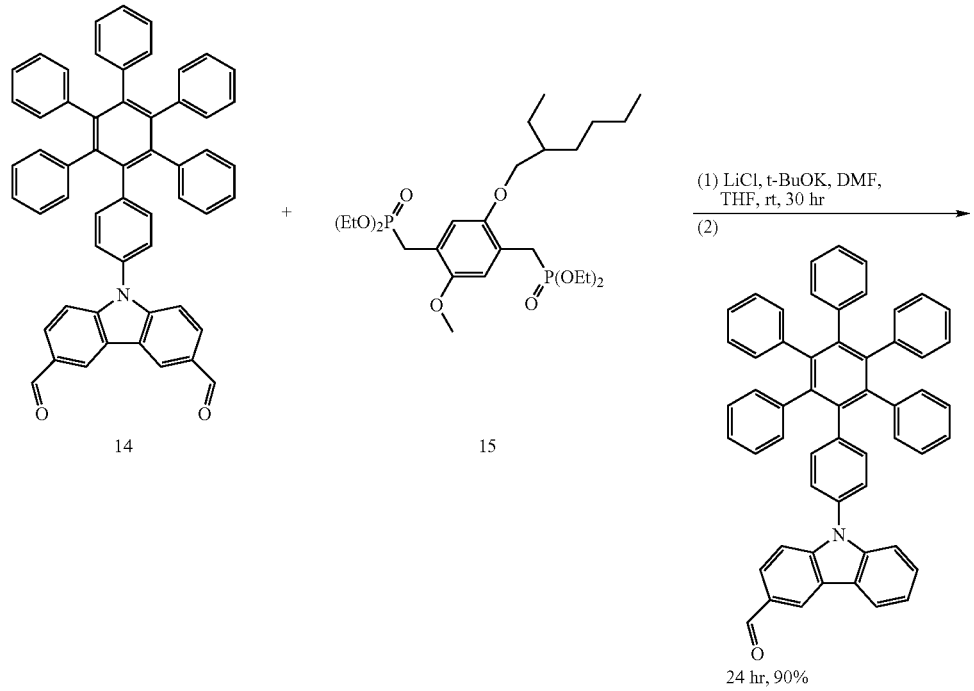

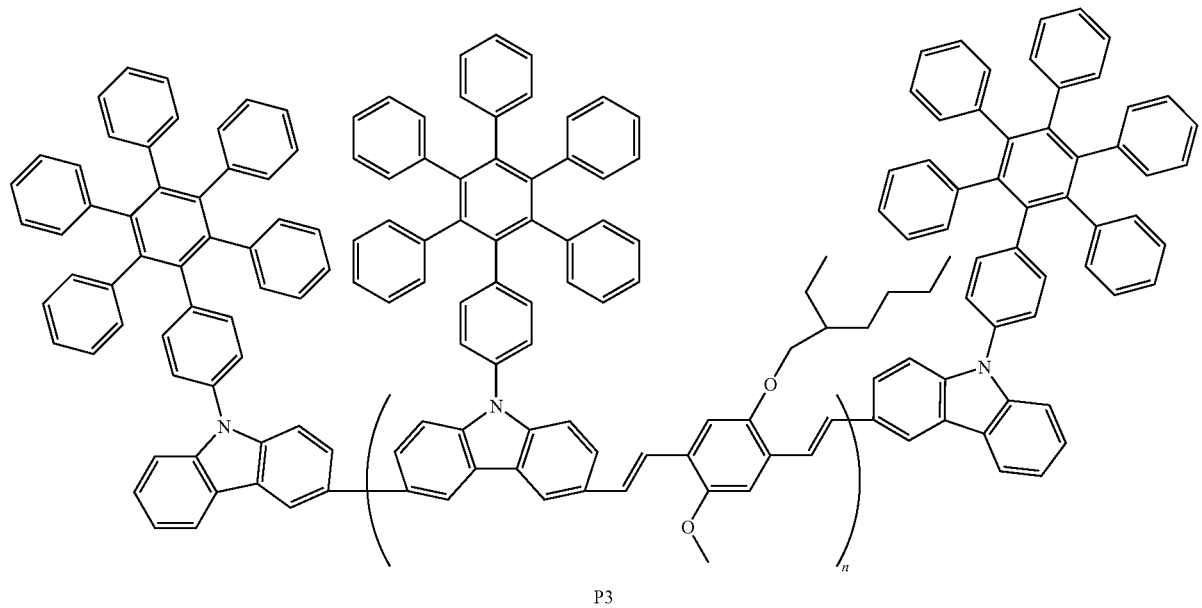

P3 material emits green light. After doped with the guest material Ir(ppy)₃, the brightness reaches 2700 cd/m² and the maximum luminance efficiency is 5.2 cd/A. The characteristics of the devices V and VI are shown in Table 6.

TABLE 6

| Device | Threshold voltage (V) | Max. Brightness (cd/m²) | Max. efficiency (cd/A) |
|---|---|---|---|
| V | 5.5 | 910 | 1.15 |
| VI | 11 | 2650 | 5.2 |

This embodiment also discloses a method for forming 9-[(pentaphenyl)phenyl]carbazole. At first a carbazole compound and a dihalo compound are provided, each having the following general equation:

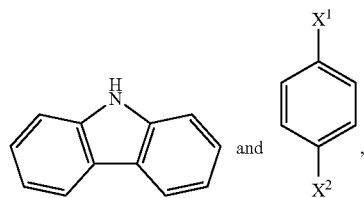

respectively, in which $X^1$ and $X^2$ can be the same or different and $X^1$ and $X^2$ are independently selected from the group consisting of the following: chlorine (Cl), bromine (Br), and iodine (I). Then, a substitution reaction between the carbazole and the dihalo compound is carried out to form a first intermediate having the following structural equation:

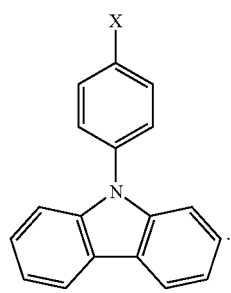

Next, a Sonogashira coupling reaction between phenylacetylene and the first intermediate is carried out to form a second intermediate having the following general equation:

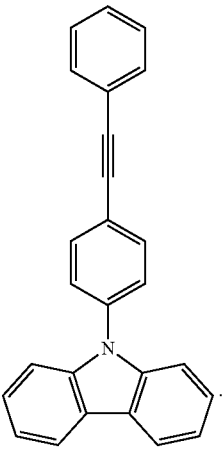 [SMILES: C(#Cc1ccc(-n2c3ccccc3c3ccccc32)cc1)c1ccccc1]

Finally, a Diels-Alder reaction between tetraphenylcyclopentadienone (TPCDO) and the second intermediate is carried out to form 9-[(pentaphenyl)phenyl]carbazole having the following general equation:

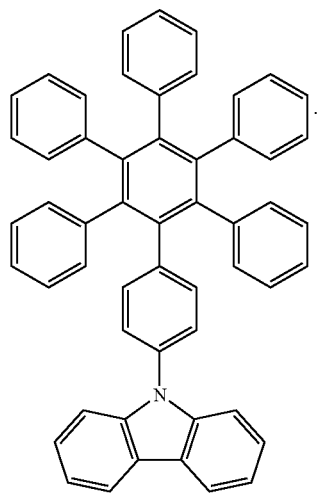 [SMILES: c1ccc(-c2c(-c3ccccc3)c(-c3ccccc3)c(-c3ccc(-n4c5ccccc5c5ccccc54)cc3)c(-c3ccccc3)c2-c2ccccc2)cc1]

Example 7

As shown in scheme 6, at first the compound 1 is formed by salt catalyzed reaction. The Sonogashira coupling reaction between the compound 1 and phenylacetylene is carried out to form the compound 2. Then, a Diels-Alder reaction between tetraphenylcyclopentadienone (TPCDO) and the compound 2 is carried out to form the compound 3. Finally, the compound is dissolved in THF to have bromination reaction with NBS. The 3,6-di-bromo-9-[(pentaphenyl)phenyl] carbazole 4 is thus formed.

The spectra data of the compound 3 is as follows:
mp 329° C.-332° C.; ¹H NMR (400 MHz, CDCl₃) δ 6.85~7.02 (m, 31H), 7.23 (t, 2H), 7.32 (t, 2H), 8.06 (t, 2H); ¹³C NMR (400 MHz, CDCl₃) δ 109.60, 119.57, 120.12, 123.97, 125.28, 125.32, 125.43, 125.59, 125.67, 126.63, 126.80, 131.41, 131.53, 134.425, 140.35, 140.40, 140.43, 140.47, 140.49, 140.92.

The spectra data of the compound 4 is as follows:
mp >380° C.; ¹H NMR (400 MHz, CDCl₃) δ 6.82~6.94 (m, 29H), 7.01 (d, 2H), 7.41 (d, 2H), 8.10 (s, 2H); ¹³C NMR (400

MHz, CDCl$_3$) δ 111.34, 112.75, 123.04, 123.65, 125.34, 125.37, 125.45, 126.66, 126.7, 126.82, 129.18, 131.36, 131.5, 132.99, 133.49, 139.87, 140.25, 140.31, 140.36, 140.44, 140.47, 141.23.
Scheme 6
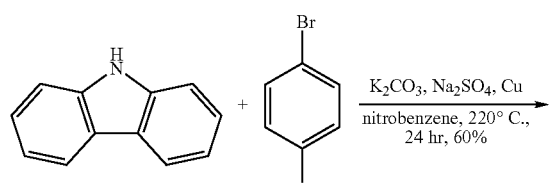
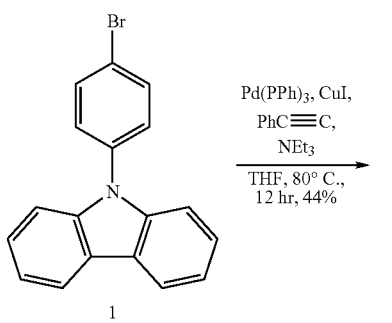
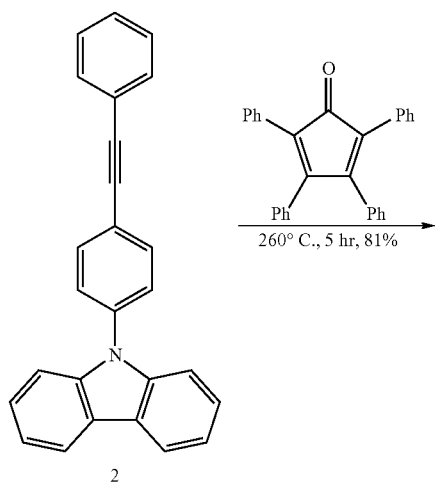
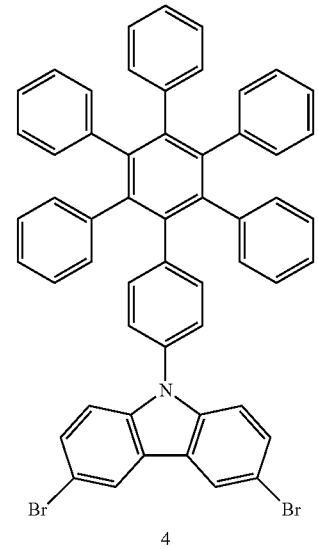 [SMILES: Brc1ccc2c(c1)c1cc(Br)ccc1n2-c1ccc(-c2c(-c3ccccc3)c(-c3ccccc3)c(-c3ccccc3)c(-c3ccccc3)c2-c2ccccc2)cc1]
4
Example 8
As shown in scheme 7, at first the compound 3 is dissolved in dichloroethane. After POCL$_3$ is dissolved in THF, it is then added into the solution of the compound 3 at 0° C. The reaction is carried out at 90° C. for 50 hrs. The compound 14 is obtained, having the following spectra data:
mp >380° C.; $^1$H NMR (400 MHz, CDCl$_3$) δ 6.85~7.09 (m, 29H), 7.94 (d, 2H), 8.64 (d, 2H), 10.11 (s, 2H); $^{13}$C NMR (400 MHz, CDCl$_3$) δ88.
Scheme 7
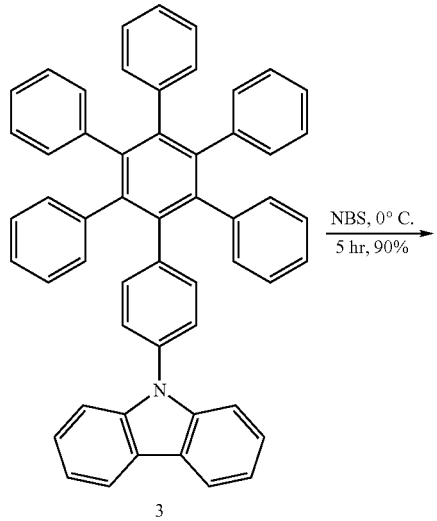
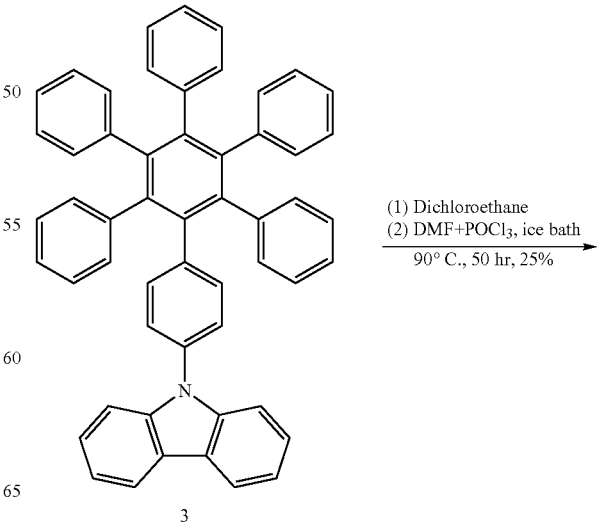

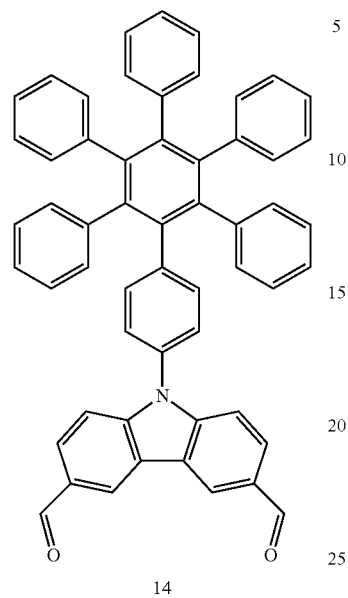

14

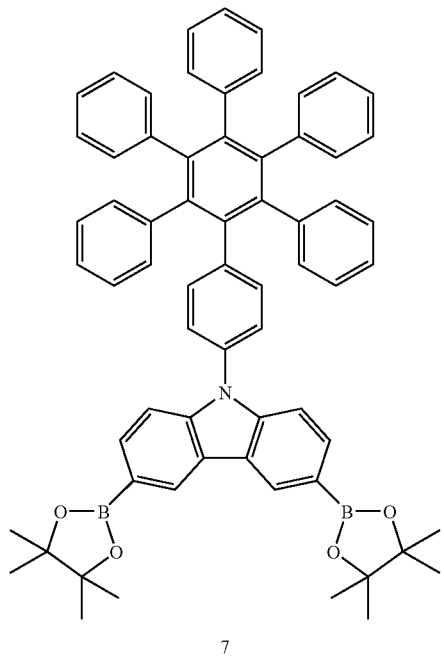

7

Example 9

As shown in scheme 8, the compound 4 dissolved in THF at −78° C. reacts with n-butyl lithium reagent and then reacts with 2-isoproxy-4,4,5,5-tetrametyl-1,3,2-dioxaborolan to obtain diborate compound 7.

Example 10

As shown in scheme 9, a Suzuki coupling reaction between the compound 4 and 1-boronic acid 4-methoxy-benzene is carried out and then hydrolysis takes place to obtain dihydroxy compound.

Scheme 8

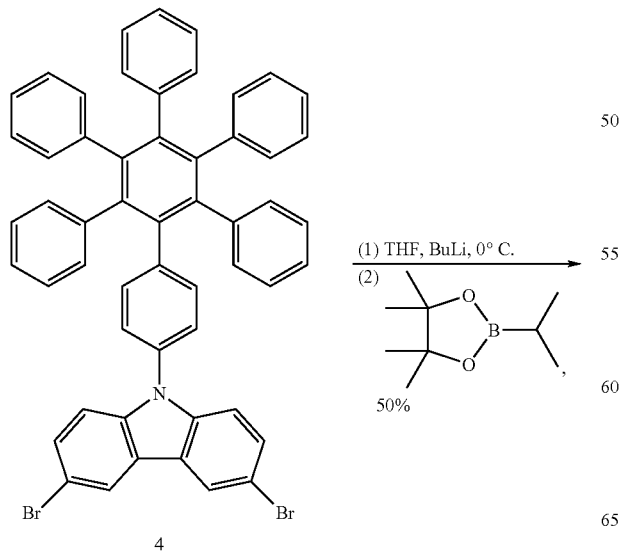

Scheme 9

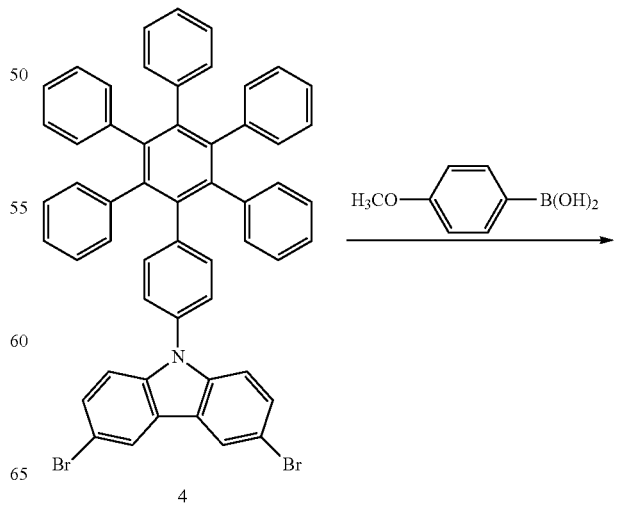

-continued

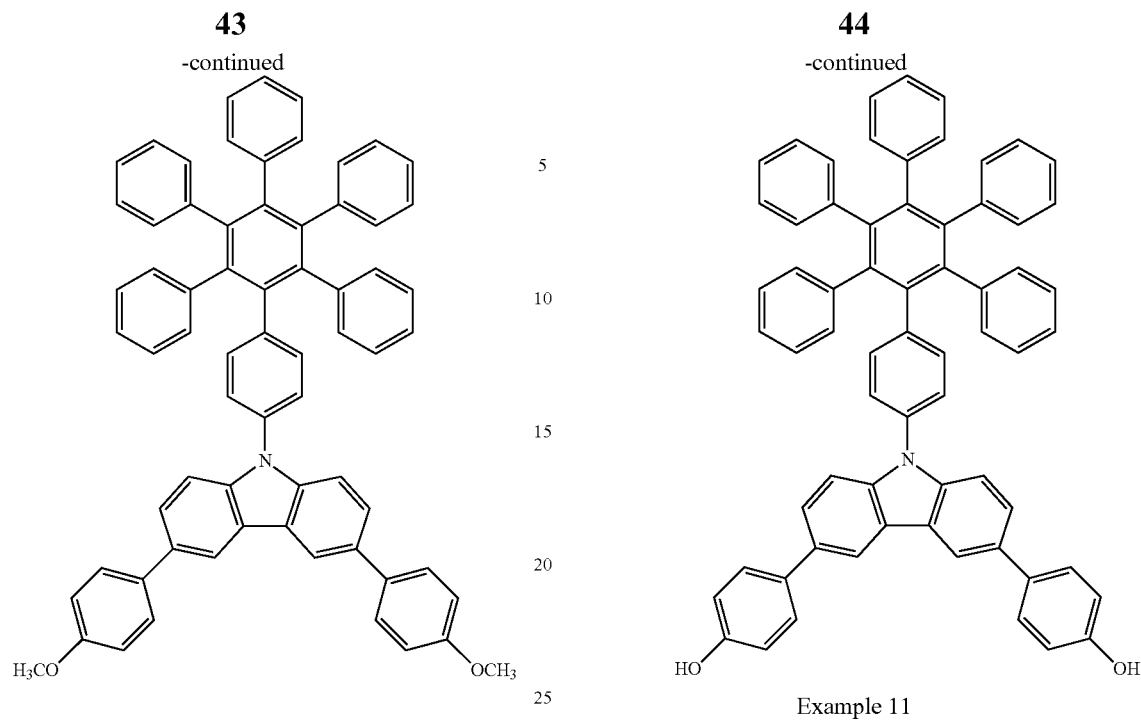

Example 11

As shown in scheme 10, a Suzuki coupling reaction between the diborate compound 7 and 1-chloro-4-vinylbenzene is carried out to obtain the compound with double bond. Such compound having double bond can be utilized in the proceeding reaction without addition of any solvent. Therefore, it does not endanger the environment and produce air pollution. In addition, it has the advantages of mild reaction condition (normal temperature and normal pressure), fast reaction rate, high transformation rate, cost effective. Thus, the product provide by this embodiment does have high commercial value.

Scheme 10

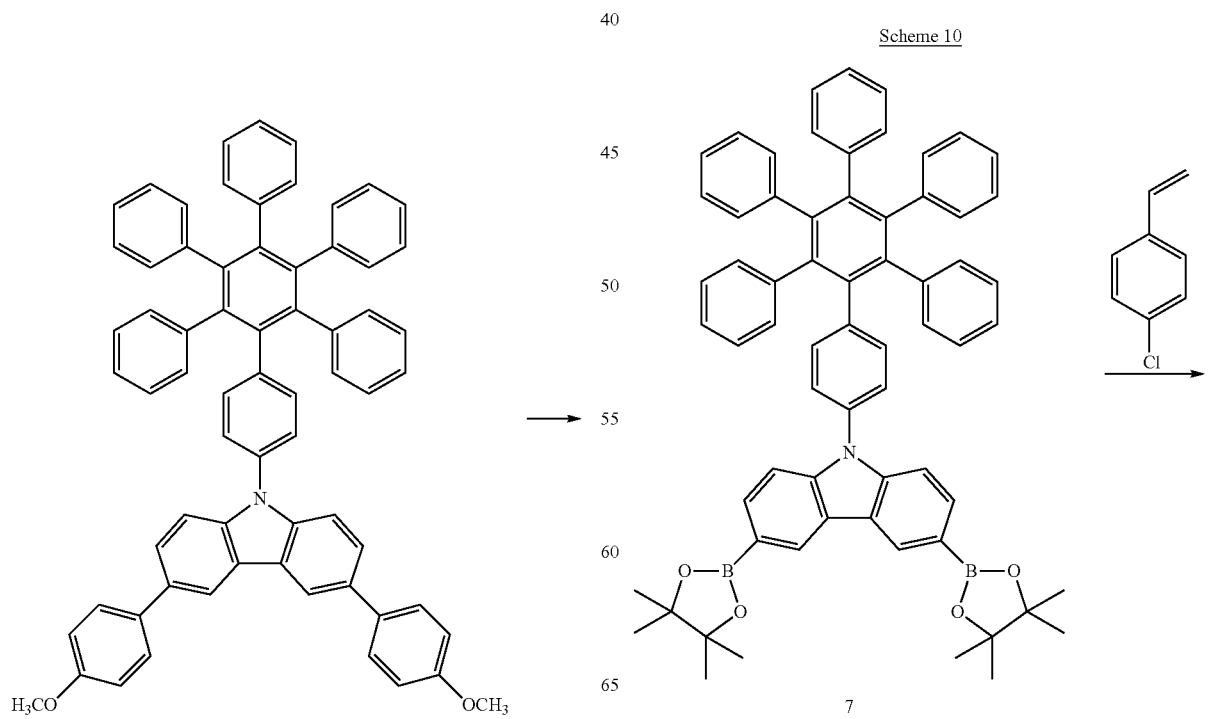

-continued

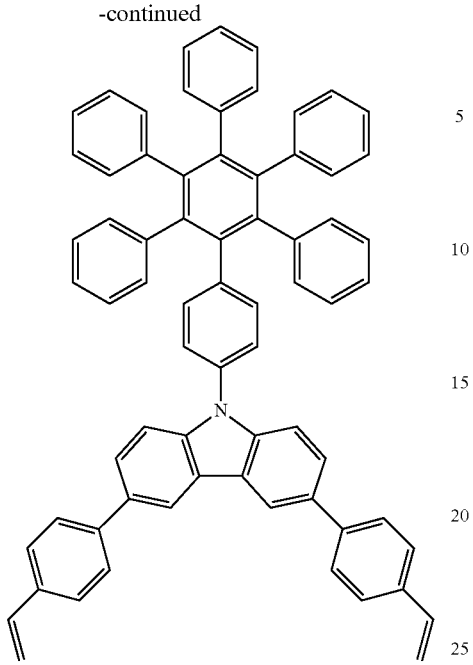

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A polymer derived from a 9-[(pentaphenyl)phenyl]carbazole structure, formed by a reaction between a compound with a 9-[(pentaphenyl)phenyl]carbazole structure according, and at least one reactive monomer, wherein said compound has the following general equation:

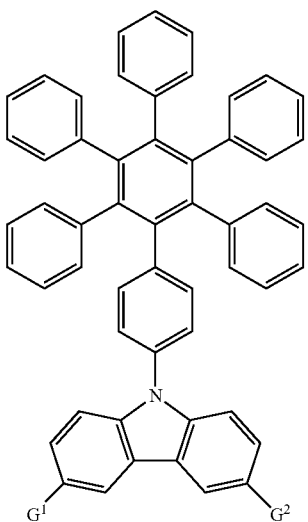

in which $G^1$ and $G^2$ can be the same or different and $G^1$ and $G^2$ are independently selected from the group consisting of the following: halogen atom,

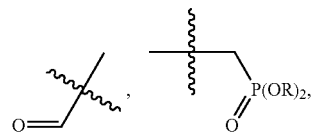

—B(OR)$_2$, and

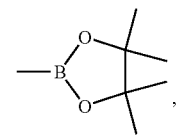

and wherein said reactive monomer is selected from the group consisting of the following:

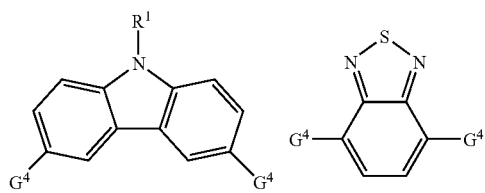

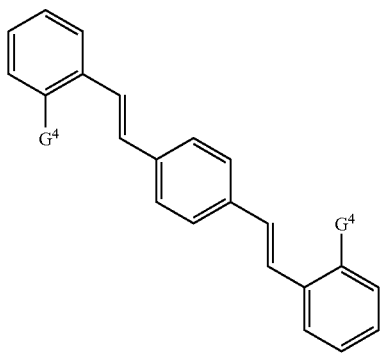

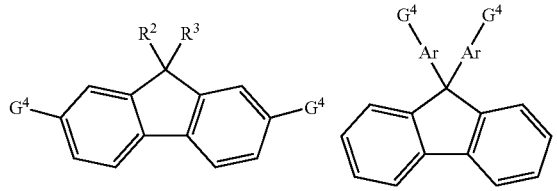

-continued

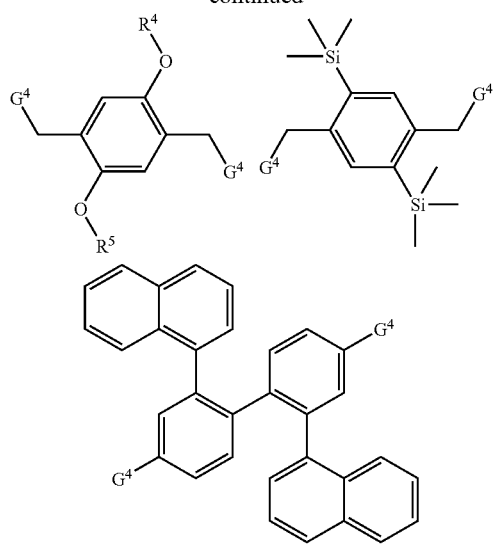

in which $R^1$, $R^2$, $R^3$, $R^4$, and $R^5$ are independently selected from the group consisting of the following: alkyl group and aryl group, $G^4$ is a halogen atom, —$B(OR)_2$,

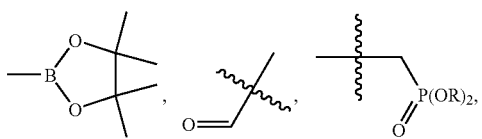

wherein R is a hydrogen atom, alkyl group, or aryl group.

2. The polymer according to claim 1, wherein said polymer derived from a 9-[(pentaphenyl)phenyl]carbazole structure is utilized in an organic solar cell device.

3. The polymer according to claim 1, wherein said polymer is utilized in an organic electroluminescence device and/or phosphorescence device.

4. The polymer according to claim 3, wherein said polymer is used as a hole injection material, hole transport material, emitting material or host material in an organic electroluminescence device and/or phosphorescence device.

* * * * *